United States Patent [19]
Hope et al.

[11] Patent Number: 6,136,597
[45] Date of Patent: Oct. 24, 2000

[54] RNA EXPORT ELEMENT

[75] Inventors: Thomas J. Hope, Encinitas; Romain Zufferey, La Jolla, both of Calif.; Didier Trono, Collonge-Bellerive, Switzerland; John Edward Donello, Cardiff, Calif.

[73] Assignee: The Salk Institute for Biological Studies, La Jolla, Calif.

[21] Appl. No.: 08/936,476

[22] Filed: Sep. 18, 1997

[51] Int. Cl.[7] .............................. C12N 5/10; C12N 1/00; C12N 15/11; C12N 15/63
[52] U.S. Cl. ...................... 435/325; 435/243; 435/320.1; 435/410; 536/24.1
[58] Field of Search ................ 536/24.1; 435/328.1, 435/325, 410, 243

[56] References Cited

U.S. PATENT DOCUMENTS 5,585,263  12/1996  Hammarskjold et al. ............... 435/236
5,637,463  6/1997  Dalton et al. ................................ 435/6

OTHER PUBLICATIONS

Huang et al., "Cellular Proteins Than Bind to the Hepatitis B Virus Posttranscriptional Regulatory Element", *Virology*, 1996, vol. 217, pp. 573–581.

Heapy et al., "HIV–1 Regulatory of Virion Expression (Rev) Protein Binds to an RNA Stem–Loop Structure Located within the Rev Response Element Region," *cell*, Feb. 23, 1990, vol. 342, pp. 686–687.

Zapp et al. "Sequence–Specific RNA Binding by the HIV–1 Rev Protein," *Nature*, Dec. 7, 1989, vol. 342, pp. 714–716.

Galibert et al., "Nucleotide Sequence of a Cloned Woodchuck Hepatitis Virus Genome:Comparision with the Hepatitis B Virus Sequence," *Journal of Virology*, Jan. 1982, vol. 41, No. 1, pp. 51–65.

*Primary Examiner*—Terry McKelvey
*Attorney, Agent, or Firm*—Gary Cary Ware & Freidenrich LLP; Lisa A. Haile

[57] ABSTRACT

A cis-acting posttranscriptional regulatory element (PRE) useful for efficient RNA export of RNA is provided. The element termed WPRE, is originally derived from woodchuck hepatitis virus. The invention also provides a method for enhancing the expression of transgenes by insertion of the WPRE nucleic acid sequences in operably linkage with the transgene.

14 Claims, 18 Drawing Sheets aatcaacctctggattacaaatttgtgaaagattgactgtattcttaactat
gttgctccttttacgctgtggatacgctgctttaatgcctttgtatcatgct
attgcttcccgtatggctttcattttctcctcctgtataatcctggttgctg
tctctttatgaggagttgtggccgttgtcaggcaacgtggcgtggtgtgcact
gtgtttgctgacgcaaccccactggttggggcattgccacctgtcagctc
ctttccggactttcgcttccccctcccctattgccacggCGGAACTCATCG
CCGCCTGCCTTGCCCGCTGGACAGGGGCTCGGCTGTGTTGGGCACTG
ACAATTccgtggtgttgtcggggaagctgacgtccttccatgctgctcgcc
tgtgttgccacctggattctgcgcgggacgtccttctgctacgtccctcggcc
ctcaatccagcgaccttcctccccgcgcctcctcgctcgcgcctctt
ccgcgtcttcgccttcbccctcagacgagtcggatctccctttggccgcctcc
ccgcctg (SEQ ID NO:1)

FIG. 1C

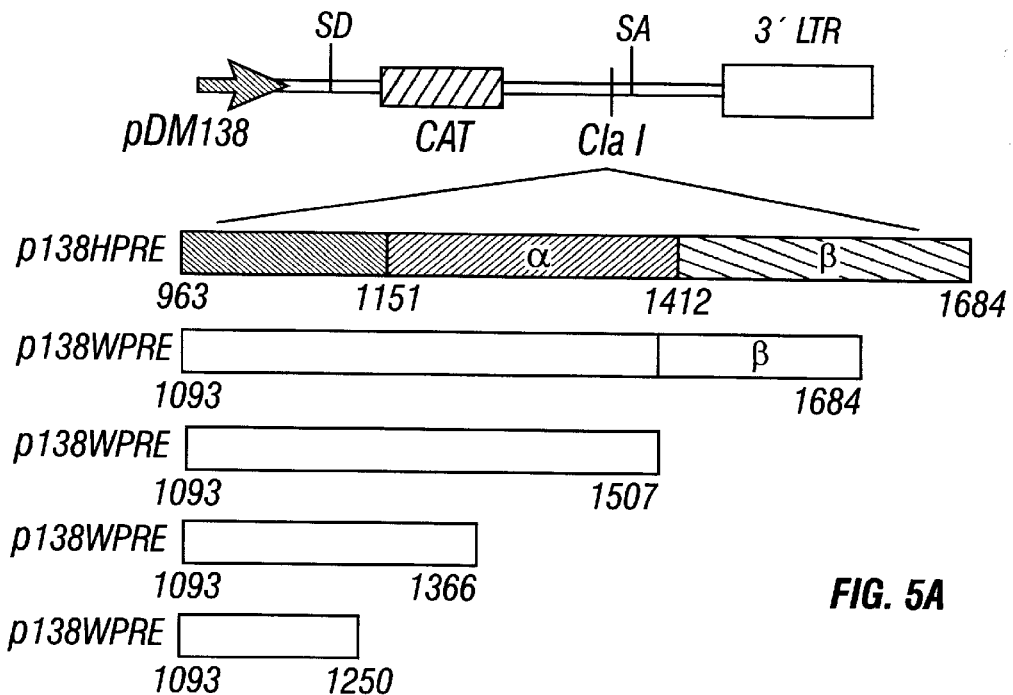
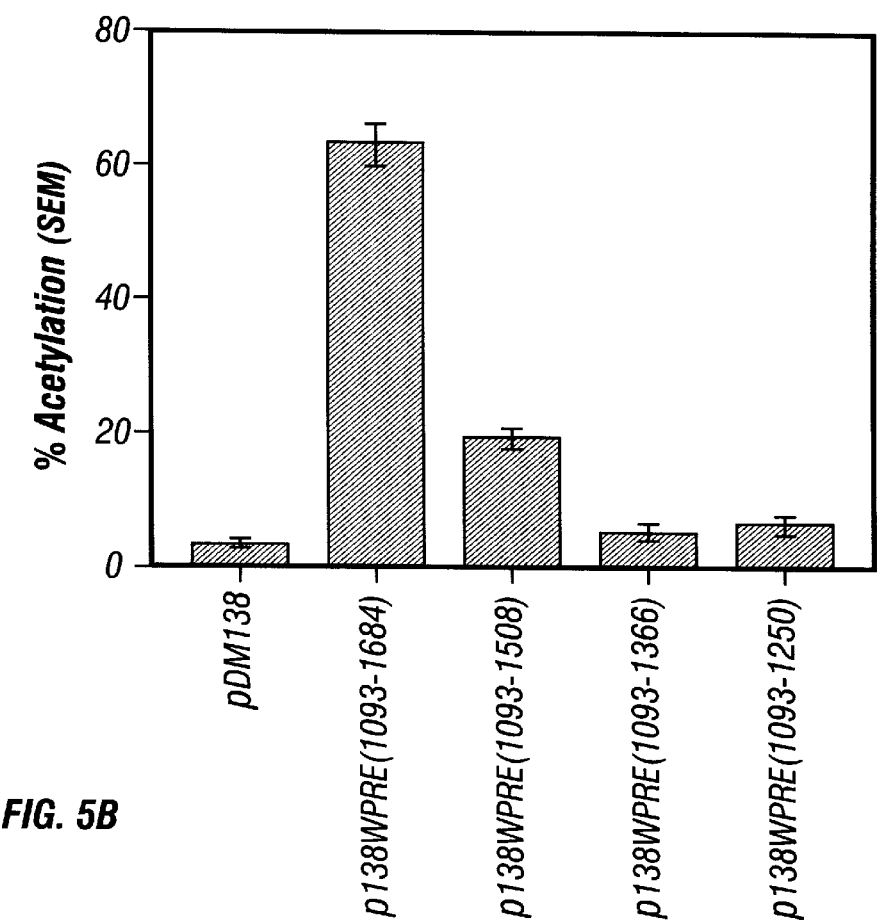
FIG. 5A
FIG. 5B (SEQ ID NO:2)

pHR'cmvGFP WHV        pHR'cmvGFP

SEQUENCE LISTING

<160> NUMBER OF SEQ ID NOS: 3

<210> SEQ ID NO 1
<211> LENGTH: 592
<212> TYPE: DNA
<213> ORGANISM: Marmota monax

<400> SEQUENCE: 1

| aatcaacctc tggattacaa aatttgtgaa agattgactg atattcttaa ctatgttgct | 60 |
| ccttttacgc tgtgtggata tgctgcttta atgcctctgt atcatgctat tgcttcccgt | 120 |
| acggctttcg ttttctcctc cttgtataaa tcctggttgc tgtctcttta tgaggagttg | 180 |
| tggcccgttg tccgtcaacg tggcgtggtg tgctctgtgt ttgctgacgc aaccccact | 240 |
| ggctggggca ttgccaccac ctgtcaactc ctttctggga ctttcgcttt ccccctcccg | 300 |
| atcgccacgg cagaactcat cgccgcctgc cttgcccgct gctggacagg ggctaggttg | 360 |
| ctgggcactg ataattccgt ggtgttgtcg gggaagctga cgtcctttcc atggctgctc | 420 |
| gcctgtgttg ccaactggat cctgcgcggg acgtccttct gctacgtccc ttcggctctc | 480 |
| aatccagcgg acctcccttc ccgaggcctt ctgccggttc tgcggcctct cccgcgtctt | 540 |
| cgctttcggc ctccgacgag tcggatctcc ctttgggccg cctccccgcc tg | 592 |

<210> SEQ ID NO 2
<211> LENGTH: 15
<212> TYPE: DNA
<213> ORGANISM: Artificial Sequence
<220> FEATURE:
<223> OTHER INFORMATION: oligonucleotides for PCR

<400> SEQUENCE: 2

| gcgggatcca tcgat | 15 |

<210> SEQ ID NO 3
<211> LENGTH: 107
<212> TYPE: RNA
<213> ORGANISM: Marmota monax

<400> SEQUENCE: 3

| uuccccucc cuauugccac ggcggaacuc aucgccgccu gccuugcccg cugcuggaca | 60 |
| ggggcucggc uguugggcac ugacaauucc gugguguugu cggggaa | 107 |

RNA EXPORT ELEMENT

STATEMENT AS TO FEDERALLY SPONSORED RESEARCH

This invention was made in part with support from grant number T32 CA 64041 from the National Institutes of Health. The government may have certain rights in this invention.

FIELD OF THE INVENTION

This invention relates generally to gene expression and more specifically to a cis-acting RNA export element and methods of use of the element for increasing expression of transgenes.

BACKGROUND OF THE INVENTION

The Hepadnaviradae family consists of closely related, yet species specific, DNA viruses which replicate via reverse transcription. Studies of human Hepatitis B Virus (HBV) and Woodchuck Hepatitis Virus (WHV) have shown that both viruses are mainly hepatotropic and contain four open reading frames that encode the major viral proteins: Core, Polymerase, Surface and X. The two viruses share approximately 59% nucleotide identity and have similar physical maps (Galibert et al., *J. Virol.* 41:51–65,1982). Although spliced HBV RNAs have been reported, the major HBV and WHV proteins are translated from unspliced RNAs. The viral RNAs terminate at the same polyadenylation site and share a common 3'termini.

The correlation of HBV infection with an increased risk of hepatocellular carcinoma has stimulated research into virus-host interactions and gene regulation of the Hepadnaviradae. Transcription of the major viral proteins is mediated by four promoters which are partially regulated by HBV enhancers I and II. HBV enhancers I and II have been shown to upregulate heterologous promoters and are believed to be key determinants of HBV hepatotropism. Both enhancer I and II are liver specific, although enhancer I retains low activity levels in some non-hepatic cells. HBV enhancer I maps upstream of the X open reading frame and consists of a modulatory domain, a core enhancer domain and a basal X promoter domain. Enhancer II maps to Core promoter region and is thought to influence levels of genomic RNA.

The transcriptional regulatory elements of WHV are not well characterized. Mapping studies have confirmed that WHV contains promoters analogous to the major HBV promoters (i et al., *Virology*, 229:25–35, 1997; Sugata et al., *Virology* 205:314–320, 1994). Recent studies have shown that WHV enhancer II is a strongly liver specific enhancer that regulates the production of pregenomic RNAs, which is an important rate limiting step of hepadnaviral replication. Surprisingly, the WHV region homologous to HBV enhancer I lacks enhancer activity in the three human liver cell lines tested. This region failed to activate transcription of the four viral promoters and did not effect a heterologous thymidine kinase promoter. The authors suggest that either the human liver cells do not express the required transcription factors or that major differences exist in the transcriptional control of HBV and WHV.

The HBV Posttranscriptional Regulatory Element (HPRE) is an orientation dependent cis-acting RNA element that partially overlaps with Enhancer I and is required for the cytoplasmic localization of HBV Surface RNAs. The HPRE does not require a virally encoded protein and is believed to interact with cellular proteins which mediate export of the intronless Surface RNA. The HPRE can functionally substitute for the HIV-1 Rev/Rev Responsive Element (RRE) complex in a transient transfection reporter assay.

In most cases, cellular mRNAs contain introns that are removed by splicing before transport to the cytoplasm occurs. Transport to the cytoplasm is required for the mRNA to interact with the ribosomes and accessory factors in the process of protein synthesis. Recent studies have suggested that intron-containing RNAs are usually prevented from exiting the nucleus due to the binding of splicing factors (Chang and Sharp, *Cell* 59:789–795, 1989; Legrain and Rosbash, *Cell* 57:573–583, 19989); although there are a few examples of differentially spliced cellular transcripts that are transported with a retained intron. Little is know about the mechanisms that allow these mRNAs to be transported.

The first identified and best characterized viral export system is the HIV-1 Rev/RRE complex (U.S. Pat. No. 5,585,263). HIV-1 Rev has been shown to directly mediate RNA export via its nuclear export signal (NES). A number of simple retroviruses, such as the Mason Pfizer Monkey Virus (MPMV), also encode cis-acting RNA export elements. MPMV encodes a structured RNA element required for the export of the intron-containing genomic RNA. An additional element has been found in the thymidine kinase (tk) gene of the Herpes Simplex Virus-1 (HSV-1). It has also been reported that hnRNP L binds to a site within the tk gene, and using mutants of the tk gene, showed a correlation between hnRNP L binding and RNA export. All of the cis-acting elements are essential for the cytoplasmic localization of viral RNA and, with the exception of the complex retroviral elements, are thought to interact with cellular RNA export proteins.

High levels of transgene expression are desired in most protocols of gene therapy. Gene delivery systems utilized for this purpose include retroviral vectors, adenoviral vectors, vectors derived from the adeno-associated virus and from herpes virus, as well as non-viral vectors. Retroviral vectors, in particular, can only transfer sequences as cDNAs instead of complete intron-containing genes, because efficient introns are spliced out during the sequence of events leading to the formation of the retroviral particle. Introns mediate the interaction of primary transcripts with the splicing machinery. Because the processing of RNAs by the splicing machinery facilitates their cytoplasmic export, due to a coupling between the splicing and transport machineries, cDNAs are often inefficiently expressed.

SUMMARY OF THE INVENTION

The present invention provides an RNA export element which mediates efficient transport of RNA from the nucleus to the cytoplasm. This RNA export element is useful for enhancing the expression of transgenes by insertion of this cis-acting nucleic acid sequence, with a transgene such that the element and the transgene are contained within a single transcript. The RNA export element described herein was derived from the woodchuck hepatitis virus (WHV). The present invention provides data showing that when the export element is present in the sense orientation, transgene expression is increased up to 7 to 10 fold as compared to the expression of genes which did not contain the RNA export element of the invention. The term "woodchuck posttranslational regulatory element" or "WPRE" is used to refer to the RNA export element of the invention. The RNA export element of the invention functions with any RNA species, including intronless RNA; spliced RNA; and unspliced RNA, for example.

In a first embodiment, the invention provides an isolated nucleic acid sequence characterized as a cis-acting RNA export element which mediates transport of RNA from the nucleus to the cytoplasm, provided that the element is not a retroviral export element (e.g., Rev). The element is defined by SEQ ID NO:1, and nucleic acid sequences complementary thereto, and contains three sub-elements termed PREα, PREβ, and PREγ. The element is useful for enhancing expression of a transgene or increasing the cytoplasmic concentration of a nucleic acid (e.g., antisense). Therefore, in another embodiment, the invention provides a method for enhancing gene expression or increasing the cytoplasmic concentration of a nucleic acid in a cell comprising operably linking the a cis-acting RNA export element of the invention to a heterologous nucleic acid sequence, wherein the cis-acting RNA export element enhances nuclear to cytoplasmic transport of the resulting mRNA transcript, thereby resulting in enhanced expression. Transgenes that may be employed in the invention include heterologous nucleic acids which encode therapeutic polypeptides (e.g., growth factors, interleukins, coagulation cascade factors) or heterologous nucleic acids which are antisense molecules.

In another embodiment, the invention provides a method for identifying a cellular protein which binds to a cis-acting RNA export element or at least one subelement which mediates transport of RNA. The method includes incubating the export-element or a cell containing the export element operably linked to a heterologous DNA or mRNA, with a suspected binding protein; separating the resulting complex of the export element and the binding protein from unbound export element; and isolating the protein. While not wanting to be bound by a particular theory, it is believed that each of the PRE subelements may be cellular protein binding sites. The method may also be employed for identification of agents or proteins that modulate the activity of the export element. For example, one can identify agents that enhance or inhibit the activity of the element.

In yet another embodiment, the invention provides a method for identifying a cis-acting RNA export element including measuring the effect of a putative export element on the expression of a heterologous nucleic acid sequence; and selecting the element which provides a higher level of expression relative to the level of expression measured in the absence of said putative export element. Optionally, the assay for identifying a cis-acting RNA export element can include a comparison with the RNA export element of the invention in order to determine whether the putative element has equivalent, lesser or greater activity than the element of the invention.

BRIEF DESCRIPTION OF THE DRAWINGS

FIGS. 1A–1C are schematic representations of the HBV and WHV genomes. FIG. 1A illustrates the negative and discontinuous positive strands of HBV relaxed DNA shown in the center circle (bold). The HBV liver specific enhancer (HBV EnhI) and the WHV and HBV liver specific enhancer II (EnhII) are shown as darkened rectangles. The four classes of hepadnaviral RNAs are represented by the curved arrows. The RNAs encode for Core (C), pre-Surface (pre-S), Surface (S), and X proteins. The shaded region within these RNAs indicates the position of the hepatitis post-transcriptional regulatory element (HPRE). FIG. 1B is a comparison of the PRE and enhancer I regions of HBV and WHV. The darkened regions correspond to the open reading frames of the Polymerase (Pol) and X proteins. The regions containing the HPREα and HPREβ sub-elements are indicated. Homologous nucleotides are aligned and the fragments are drawn to scale. The HBV enhancer I (HBV EnhI) is indicated. FIG. 1C is the nucleotide sequence of WPRE of the invention (SEQ ID NO: 1).

FIG. 2A is a Schematic of the WPRE and HPRE p138 vectors. The fragments of HBV and WHV are labeled according to the nucleotide numbers of WHV accession #J04514 and HBV accession #D00329, respectively. Homologous nucleotides are aligned and the fragments are drawn to scale. The darkened regions correspond to the HPREα and HPREβ sub-elements. The shaded region of HPRE contains a portion of the enhancer modulatory domain and is not required for HPRE function. The filled arrow represents the simian virus 40 promoter from which the RNAs are transcribed. The chloramphenicol acetyltransferase gene (CAT) (hatched box), which is expressed only when unspliced RNA is exported, is located within the intron. The unique Cla I site is indicated. SD, splice donor. SA, splice acceptor. 3' LTR, 3' HIV-1 long terminal repeat. FIG. 2B is a comparison of the activities of HPRE and WPRE in non-liver cells. The left panel and right panel present the results from transiently transfected CV1 and Chicken Embryo Fibroblasts (CEF) cells, respectively. The labeled bars represent the average percent acetylation of triplicate transfections. The error bars are the standard error of the mean (SEM). FIG. 2C is a comparison of the HPRE and WPRE activities in liver cells. The left panel and right panel correspond to human HepG2 cells and chicken LMH cells, respectively.

FIG. 3A is a schematic representation of the pGL3 vector. The light shaded arrow represents the orientation of the inserted WPRE(1093–1684) and WPRE (963–1684) fragments. The darkened arrow represent the simian virus 40 promoter and the luciferase gene is labeled accordingly. pA, polyadenylation site. FIG. 3B shows the enhancer activity of the HPRE and WPRE. The shaded bars represent mean luciferase activity of triplicate transfections. The left panel and right panel present the results from triplicate transient transfected CV1 and HepG2 cells, respectively. RLU, relative light units.

FIG. 4A is a schematic representation of the transfected constructs. The nucleotide numbers indicate the size of the tested fragment. The other labels correspond to the description in FIG. 2A. FIG. 4B shows that the 5' end of the WPRE is sensitive to deletion. The shaded bars represent mean CAT activity of CV1 cells transfected in triplicate.

FIGS. 5A and 5B show 3' Deletion analysis of WPRE. FIG. 5A is a schematic representation of the transfected constructs. The nucleotide numbers indicate the size of the tested fragment. The other labels correspond to the description in FIG. 2A. FIG. 5B shows that the 5' end of the WPRE has minimal activity. The shaded bars represent mean CAT activity of CV1 cells transfected in triplicate.

FIG. 6A is a schematic representation of the transfected constructs. The fragments are labeled according and the nucleotide numbers are according to the Genbank submissions. The other labels correspond to the description in FIG. 2A. FIG. 6B shows that WPRE and HPRE sub-element have similar levels of activity. The shaded bars represent mean CAT activity of CV1 cells transfected in triplicate.

FIG. 7A shows the predicted structure and sequence (SEQ ID NO: 2) of the WPREα sub-element. Nucleotides 1381–1487 were analyzed by Mulfold (Jaeger et al., 1989). The boxes indicate the bases that co-vary between WHV, HBV and GSHV. The covarying base pairs in HBV and GSHV are shown. The arrows indicate the nucleotides that were mutated in FIG. 7B and 7C. FIG. 7B is a schematic representation of the transfected constructs. The fragments are labeled accordingly and the nucleotide numbers are according to the Genbank submissions. The two G residues indicate the mutations in the WPREα sub-element. The other labels correspond to the description in FIG. 2A. FIG. 7C shows that mutating the WPREα sub-element decreases WPRE activity. The shaded bars represent mean CAT activity of CV1 cells transfected in triplicate.

FIG. 8A is a schematic representation of the transfected constructs. The fragments are labeled accordingly. The chimeric elements are labeled accordingly. The HPREα (Hα), HPREβ (Hβ), WPREα (Wα), WPREβ (Wβ) and WPREγ (Wγ) sub-elements are labeled accordingly. The other labels correspond to the description in FIG. 2A. FIG. 8B shows shaded bars that represent mean CAT activity of triplicate transfections. The left panel and right panel are the results from triplicate transient transfections of CV1 and HepG2 cells, respectively.

FIG. 9A is a schematic representation of the CMV HBV Surface expression construct. The large black arrow represents the immediate early CMV promoter upstream of the HBV Surface protein open reading frame. pA, polyadenylation signal. HPRE and WPRE were cloned into the Cla I site. FIG. 9B shows that the WPRE and HPRE mediate similar levels of HBV Surface expression in CV1 and HepG2 cells. The shaded bars represent the mean counts per minute from the media of duplicate transfections. The left panel and right panel are the results from duplicate transient transfections of CV1 and HepG2 cells, respectively.

FIG. 13A shows results from 293T cells transduced with both types of vector by adding equivalent amounts of p24 on $10^5$ cells. At the level of detection chosen, many more cells appear positive when the vector contains WPRE. FIG. 13B is a FACS analysis of 293T cells transduced as in FIG. 13A. The three histograms correspond to non-transduced cells (top), cells transduced with a vector not containing WPRE (middle) or containing WPRE (bottom). The enhanced expression of GFP is reflected by the high number of cells scoring above $2 \times 10^2$ on the fluorescence scale. FIG. 13C is a graphic representation of the histograms shown in FIG. 13B. High expressors are defined as cells scoring above $2 \times 10^2$ on the fluorescence scale in FIG. 13B. The number of high expresser is 25 times higher when the vector contains WPRE.

DESCRIPTION OF THE PREFERRED EMBODIMENTS

In an effort to identify posttranscriptional regulatory elements (PREs) from Woodchuck Hepatitis Virus (WHV), the inventors mapped a putative WHVPRE (WPRE) and determined that it contained three sub-element, PREα, PREβ and PREγ. In contrast to human Hepatitis B Virus (HBV), WHV lacks the enhancer I element, however, lack of this element is overcome by increased posttranscriptional activity of WPRE. The data presented herein and in the following Examples show that nucleotides 1300–1507 of WHV encompass the minimal PREα sub-element; 1508–1684 encompass the minimal PREβ sub-element; and 1093–1250 encompass the minimal PREγ sub-element. These sub-elements likely represent distinct binding sites for cellular RNA export proteins.

The data also demonstrates that the PREα and PREβ sub-elements are evolutionarily conserved between WHV and HBV. The HPREβ sub-element was originally mapped to HBV nucleotides 1412–1684, which are homologous to WHV nucleotides 1542–1814. In FIG. 5B, the drop in activity between p138WPRE(1093–1508) and p138WPRE (1093–1250) is consistent with WPREα being contained within nucleotides 1250–1507. This fragment is homologous to HBV nucleotides 1120–1377, which encompasses the HPREα region. Finally, FIG. 6B indicates that the activities of WPREγ(1093–1250), WPREα(1300–1507), WPREβ(1508–1684), HPREα and HPREβ are comparable.

Figure 7A:
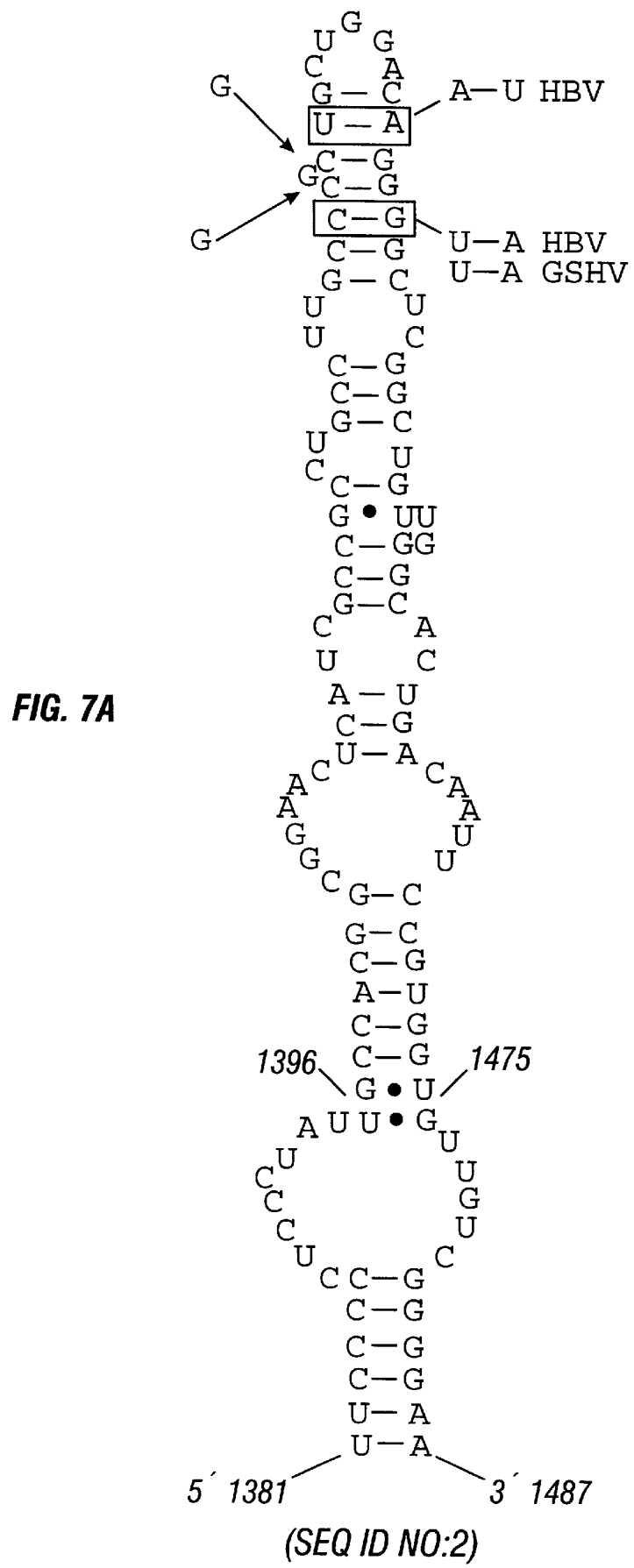
FIGS. 7A–7C show The putative structure and mutation analysis of the WPREα sub-element.
Figure 7B:
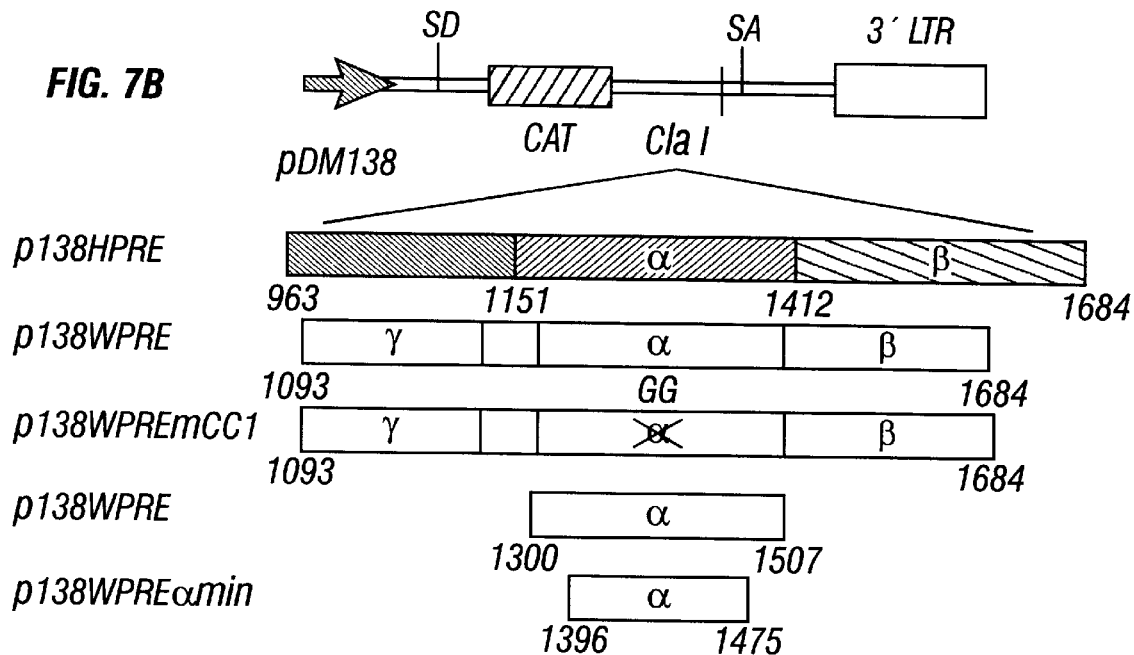
Figure 7C:
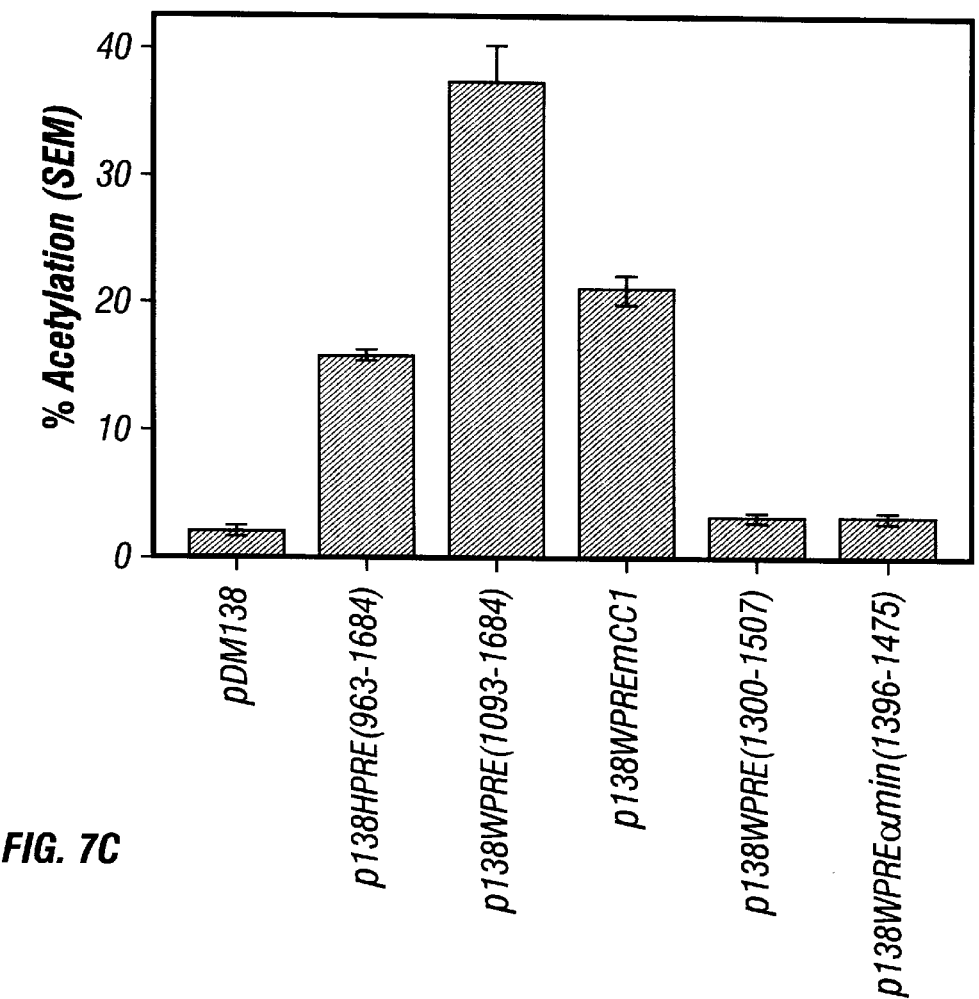

The functional conservation of the HPREα and WPREα sub-elements suggests that WPREα structure is also conserved. Phylogenetic comparative analysis highlighted two base pairs that covary within a possible stem loop structure in WPREα. Two covarying base pairs within a helix is considered nominal proof of a secondary structure model (Pace et al., 1989). RNA secondary structure predictions provided further support for the covarying bases since the lowest energy model predicted that the covarying bases were paired. FIG. 7C shows that mutating two residues within the stem decreased WPREα activity by greater than 40%. In addition, the predicted stem loop structure of WPREα, embraced by nucleotides 1396–1475, displayed the same level of activity as p138WPRE(1300–1507). These data support the hypothesis that WHV nucleotides 1396–1475 encompass the hepadnaviral PREα protein binding site.

The cellular protein(s) that interact with the WPRE and HPRE have not been identified to date. A single cellular protein may bind to each of the PRE sub-elements or, alternatively, distinct cellular proteins may bind to each of the sub-elements. The HPRE and WPRE elements are functional in each cell line tested which indicates that the PRE binding proteins are evolutionarily conserved. Functional PREα and PREβ sub-elements are conserved between the two viruses, hence PREα and PREβ binding proteins should interact with both HPRE and WPRE. The invention provides a method for identifying such PRE-binding proteins. Besides the PREα sub-element, the secondary structures of the sub-elements have not been determined however the predicted secondary structure models of PREγ, PREα and PREβ do not appear to share any striking similarities. In addition, WPREγ and WPREβ do not contain any WPREα-like secondary structures. Since the PRE sub-elements do not share my obvious similarities, it is believed that multiple cellular proteins mediate export of the hepadnaviral PREs.

Figure 2B:
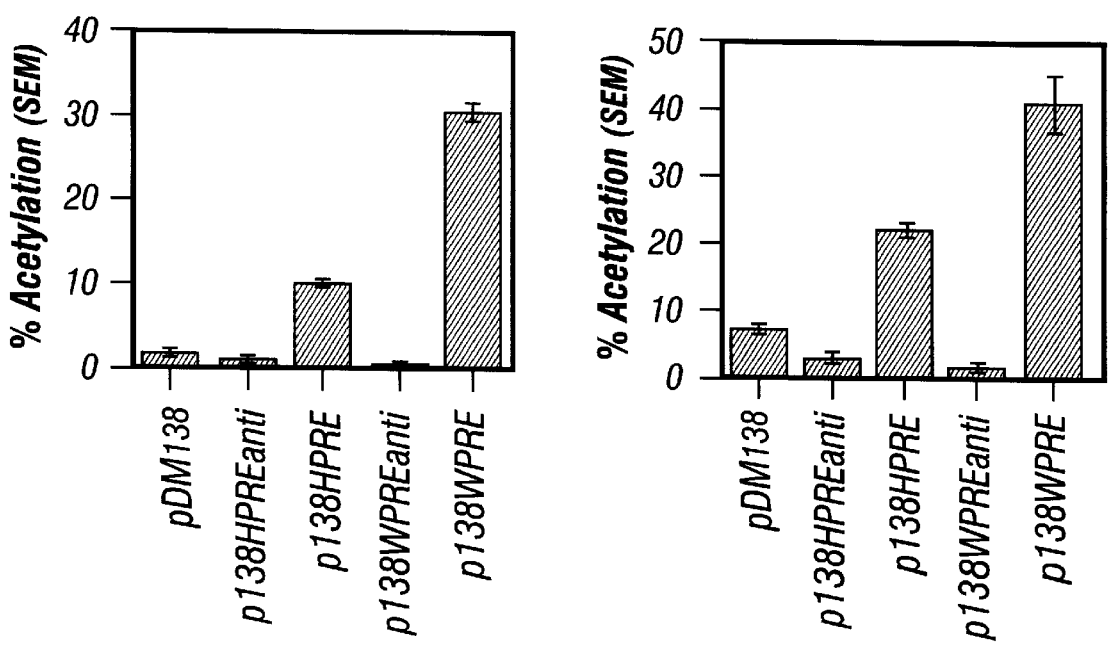
Figure 3A:
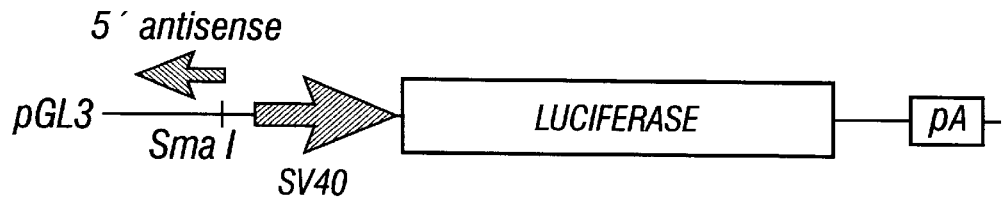
FIGS. 3A and 3B are a comparison of the WHV and HBV enhancer I activity.
Figure 3B:
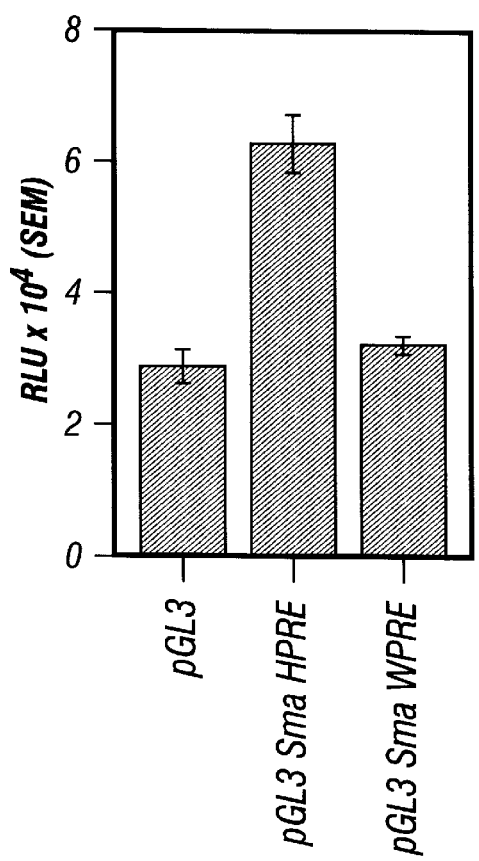
Figure 3B:
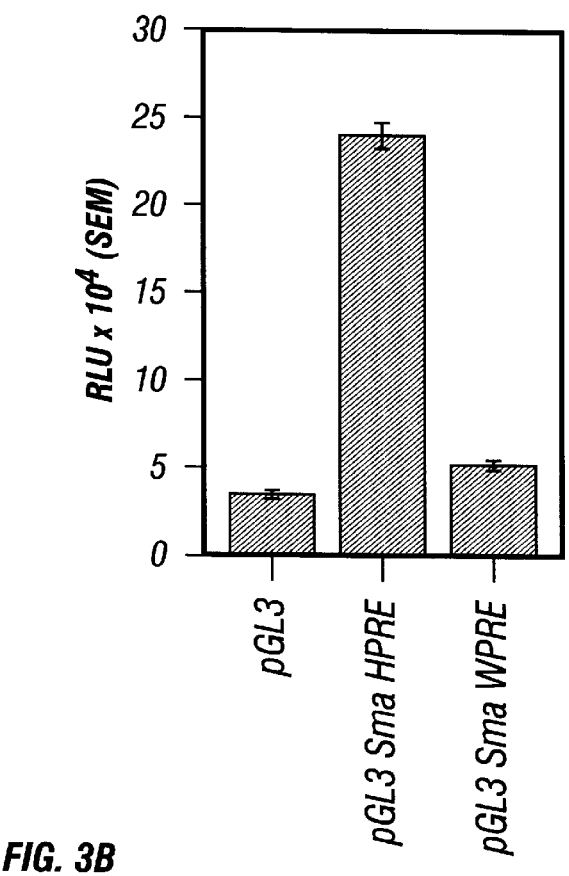

Despite their similar activities, HPRE and WPRE display distinctly different activities in a tissue dependent manner. This difference centers upon the partially liver specific enhancer I that overlaps with the HPRE. FIG. 3B corroborates previous reports that WHV lacks an enhancer homologous to HBV enhancer I (Di et al., 1997; Fourel et al., 1996; Ueda et al., 1996a). If the transcriptional effect of HBV enhancer I is considered, WPRE is stronger than the HPRE in both CV1 and HepG2 cells. For instance, the WPRE is approximately three times stronger than the HPRE in CV1 cells (FIG. 2B). If the transcription effects of enhancer I are considered, the WPRE is actually six times stronger than the HPRE. In HepG2 liver cells, the WPRE possessed 85% of the HPRE activity but the WPRE is four times stronger than the HPRE when the enhancer effects are considered. If the effect of the enhancer is factored into the Surface expression results, the WPRE is 2.8 and 3.3 fold stronger than the HPRE in CV1 and HepG2 cells, respectively. Therefore, the apparent liver specific increase of HPRE activity is most likely a transcriptional effect due to the presence of HBV enhancer I. These results indicate that distinct differences exist between the transcriptional and posttranscriptional regulation of WHV and HBV genomes.

Figure 8A:
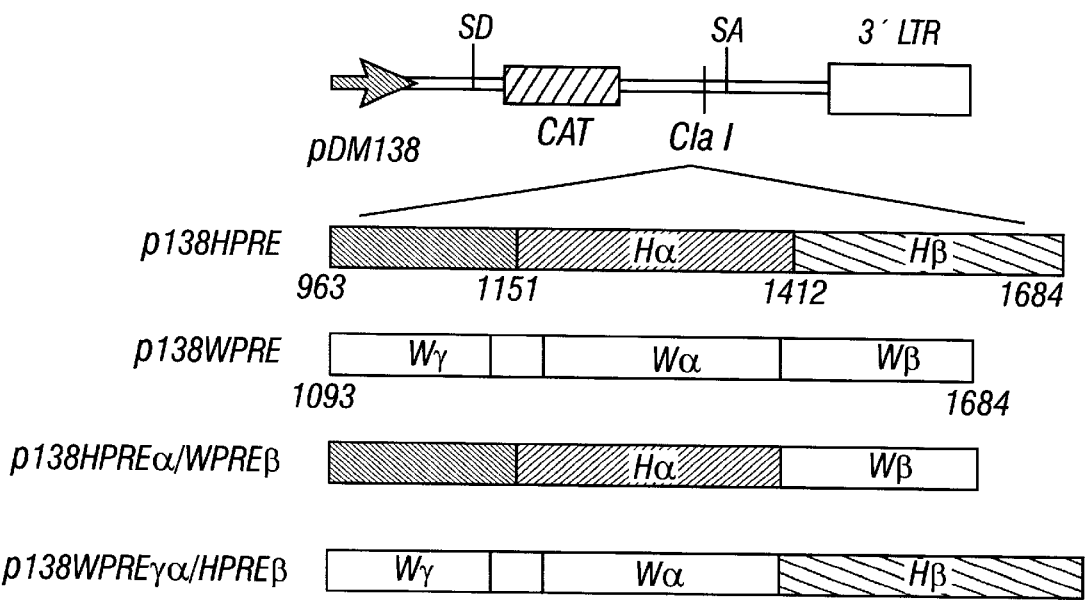
FIGS. 8A and 8B show chimeric elements of WPRE and HPRE correlate with the presence of the WPREγ or HBV enhancer I.
Figure 8B:
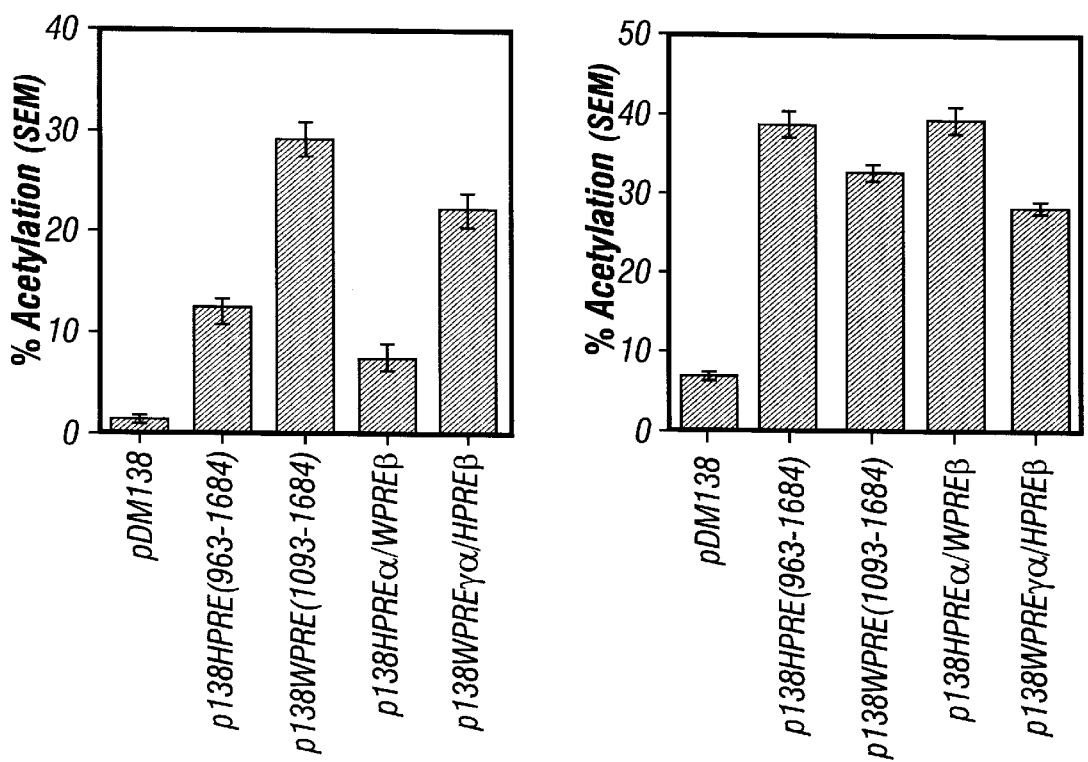

Several observations suggest that the increased posttranscriptional strength of the WPRE is due to the presence of three sub-elements. Deletion of WPREβ results in an element that displays approximately the same level of activity as the two sub-element HPRE (FIG. 5B). In addition, mutating the putative stem-loop in WPREα decreases WPRE activity to the level of the two sub-element HPRE. Furthermore, the tripartite WHVγα/HPREβ chimera is significantly stronger in CV1 cells than either the HPRE or the HPREα/WPREβ chimera, both of which are bipartite elements (FIG. 8B). These data support the hypothesis that WPRE is a tripartite element and that the stronger posttranscriptional activity is due to the presence of three sub-elements.

Figure 6A:
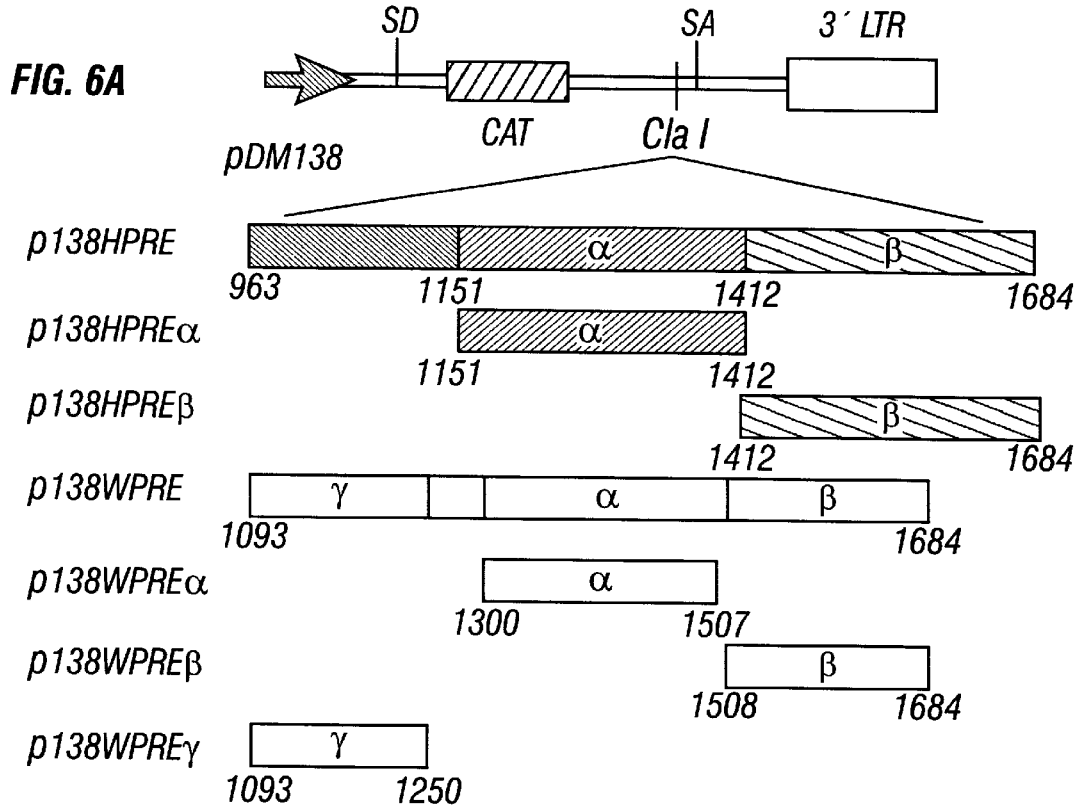
FIGS. 6A and 6B show the WPRE and HPRE sub-elements have similar levels of activity.
Figure 6B:
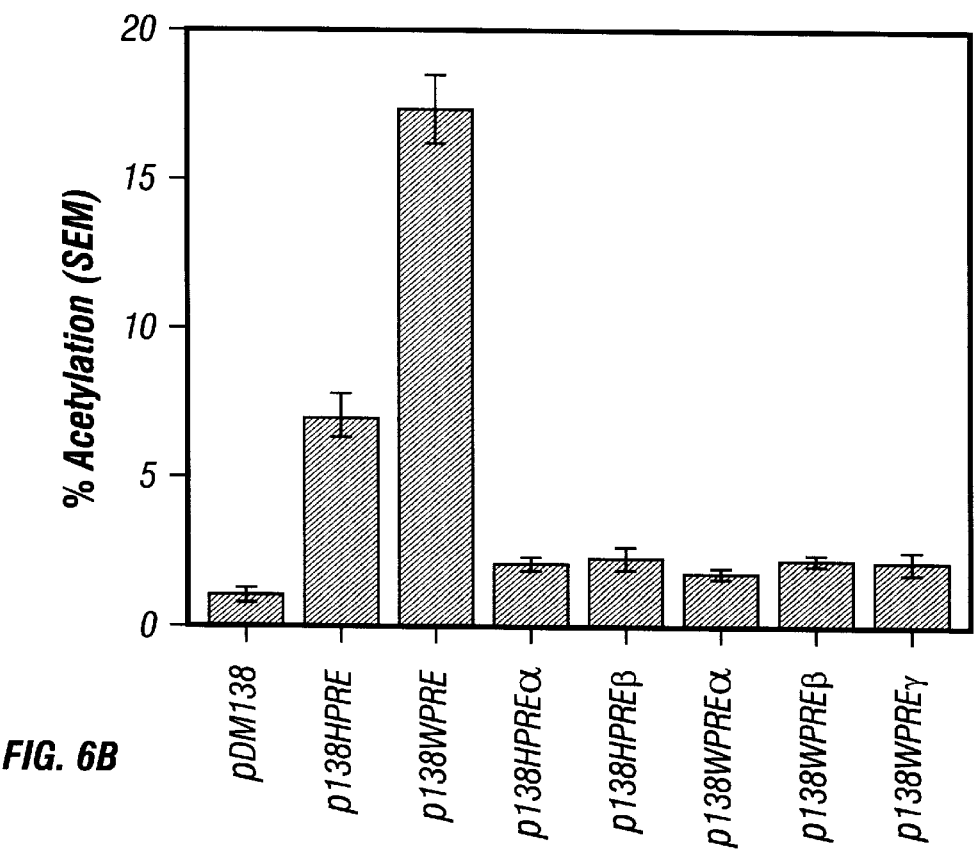

The three WPRE sub-elements function cooperatively to increase the posttranscriptional activity of the element. WPREα, WPREβ, and WPREγ each possess approximately 12% of the WPRE activity (FIG. 6B). In the context of the full-length WPRE, point mutations within WPREα, decrease WPRE activity approximately 40%. These data support the interpretation that the PRE binding proteins function cooperatively. Previous experiments have shown that HPREα and HPREβ function cooperatively with each other or with themselves when duplicated (Donello et al., 1996). These data are similar to reports that duplication of the Rev or HTLV-1 Rex high-affinity binding sites are required for wild type activity (Grone et al., 1994; Huang et al., 1991). Recent experiments by the present inventors have shown that, in the presence of Rev, the high-affinity binding site of Rev and HPRE function cooperatively to export reporter RNA. The difference in posttranscriptional activities of the bipartite HPRE and the tripartite WPRE suggest that the posttranscriptional strength of an element is determined by the number of protein binding sites within the element. These data support a model wherein the PRE export proteins function cooperatively and the efficiency of export may be modulated by the number of export proteins bound to the RNA.

The regions delineating HPRE and WPRE are obviously complex, since they contain two partially overlapping open reading frames, the X promoter, the PRE and the HBV enhancer I. Hence, it is remarkable that HV and HBV, which share an overall 59% nucleotide identity, exhibit distinct differences within this critical region. In fact, the WPREα and WPREβ subelements share approximately 66.7% nucleotide identity with HBV. The HBV core enhancer domain is almost completely conserved between the two viruses but the 5' HBV enhancer modulatory domain is more divergent (Di et al., 1997). This region, which shares only 60.7% nucleotide identity between HBV and WHV, is not required for HPRE activity but is essential for WPRE activity since it encodes the WPREγ sub-element.

The data presented indicate that the increased posttranscriptional strength of tripartite WPRE compensates for the lack of a WHV enhancer I. In CV1 cells, WPRE can activate human Surface protein expression to a level comparable with the HPRE (FIG. 9B). In HepG2 cells, WPRE can maintain slightly lower levels of human Surface protein, without the benefit of enhancer I. Hence, in the heterologous context of the HBV Surface expression construct, WPRE can functionally replace the enhancer I-containing HPRE. It has been previously shown that HBV enhancer I is preferentially active in liver cells, yet retains lower activity levels in some non-hepatic cells. In contrast the PRE is constitutively active in every cell type tested.

Definitions

The term "gene expression", as used herein, means the process by which a nucleotide sequence undergoes successful transcription and translation such that detectable levels of the corresponding protein are obtained and a functional biological effect achieved.

By "construct" is meant a recombinant nucleotide sequence, generally a recombinant DNA molecule, that has been generated for the purpose of the expression of a specific nucleotide sequence(s), or is to be used in the construction of other recombinant nucleotide sequences. In general, "construct" is used herein to refer to a recombinant DNA molecule.

"Expression construct" as used herein means a construct which has at least one WPRE sequence associated with a heterologous nucleic acid encoding a desired product, such that the nucleic acid is expressed at enhanced levels as compared to the level of expression in the absence of a WPRE sequence(s).

By "promoter" is meant the minimal DNA sequence sufficient to direct transcription of the heterologous nucleic acid sequence to which it is operably linked. The term "promoter" is also meant to encompass those promoter elements sufficient for promoter-dependent gene expression controllable for cell-type specific expression, tissue-specific expression, or inducible by external signals or agents; such elements may be located in the 5' or 3' regions of the heterologous nucleic acid or transgenes utilized herein.

By "inducible promoter" is meant a promoter that is transcriptionally active when bound to a transcriptional activator, which in turn is activated under a specific condition(s), e.g., in the presence of a particular chemical signal or combination of chemical signals that affect binding of the transcriptional activator to the inducible promoter and/or affect function of the transcriptional activator itself.

By "operably linked" or "operably associated" is meant that a DNA sequence (e.g., a heterologous nucleic acid or transgene as used herein) and a regulatory sequence(s) are associated in such a way as to permit gene expression when the appropriate molecules (e.g., transcriptional activator proteins) are bound to the regulatory sequence(s). In the present invention, regulatory sequences include promoters. Further, the term "operably linked" also refers to the linkage between the transgene and the WPRE of the invention such that the WPRE is contained within the resulting mRNA transcript.

By "operatively inserted" is meant that a nucleotide sequence of interest is positioned adjacent a nucleotide sequence that directs transcription and translation of the introduced nucleotide sequence (i.e., facilitates the production of the corresponding polypeptide encoded by the nucleotide sequence of interest).

By "transformation" is meant a permanent or transient genetic change, induced in a cell following incorporation of new DNA (i.e., DNA exogenous to the cell). Where the cell is a mammalian cell, a permanent genetic change is generally achieved by introduction of the DNA into the genome of the cell.

By "transformed cell" is meant a cell containing a DNA molecule encoding a gene product. Gene products includes RNAs and/or proteins of interest wherein the DNA is introduced into the cell by means of recombinant DNA techniques.

By "nucleotide sequence of interest," "nucleic acid of interest" or "DNA of interest" is meant any nucleotide or DNA sequence that encodes a protein or other molecule intended for expression in a host cell (e.g., for production of a protein or other biological molecule, such as a therapeutic cellular product, in the target cell. The nucleotide sequence of interest is generally operatively linked to other sequences which are needed for its expression, e.g., a promoter in addition to the WPRE of the invention. The nucleotide sequence of interest encodes the gene product of interest, usually a therapeutic gene product (e.g., in a gene therapy application in humans).

By "therapeutic gene product" is meant a polypeptide, RNA molecule or other gene product that, when expressed in a target cell, provides a desired therapeutic effect, e.g., repair of a genetic defect in the target cell genome (e.g., by complementation), expression of a polypeptide having a desired biological activity, and/or expression of an RNA molecule for antisense therapy (e.g., regulation of expression of a endogenous or heterologous gene in the target cell genome).

By "subject" or "patient" is meant any subject for which cell transformation or gene therapy is desired, including humans, cattle, dogs, cats, guinea pigs, rabbits, mice, insects, horses, chickens, and any other genus or species.

By "transgenic organism" is meant a non-human organism (e.g., single-cell organisms (e.g., yeast), mammal or non-mammal (e.g., nematode or Drosophila)) having a non-endogenous (i.e., heterologous) nucleic acid sequence present as an extrachromosomal element in a portion of its cells or stably integrated into its germ line DNA.

By "transgenic animal" is meant a non-human animal, usually a mammal, having a non-endogenous (i.e., heterologous) nucleic acid sequence present as an extrachromosomal element in a portion of its cells or stably integrated into its germ line DNA (i.e., in the genomic DNA of most or all of its cells). Heterologous nucleic acid is introduced into the germ line of such transgenic animals by genetic manipulation of, for example, embryos or embryonic stem cells of the host animal. The WPRE of the invention may be used to increase gene expression in the transgenic organism or animal.

By "vector" is meant any compound or formulation, biological or chemical, that facilitates transformation or transfection of a target cell with a DNA of interest. Exemplary biological vectors include viruses, particularly attenuated and/or replication-deficient viruses. Exemplary chemical vectors include lipid complexes and DNA constructs. By "viral vector" is meant a recombinant viral particle that accomplishes transformation of a target cell with a nucleotide sequence of interest.

"Transgene" means any piece of DNA which can be inserted into a cell, and preferably becomes part of the genome of the resulting organism (i.e., either stably integrated or as a stable extrachromosomal element). Such a transgene includes genes which are partly or entirely heterologous (i.e., foreign) as well as genes homologous to endogenous genes of the organism. Included within this definition is a transgene created by providing an RNA sequence which is reverse transcribed into DNA and then incorporated into the genome, or an antisense agent or molecule.

The term "antisense agent" refers to a molecule which interacts directly with intracellular DNA or RNA to achieve a therapeutic effect. Examples of antisense agents include, without limitation, DNA-binding molecules, triple-helix (or triplex) forming agents, ribozymes, and the like. Antisense agents may be prepared from naturally-occurring nucleotides, or may contain modified bases. The WPRE of the invention may be linked to an antisense molecule to increase its cytoplasmic concentration.

A "triplex-forming agent" is a molecule which hybridizes to a specific region of duplex DNA, typically lying in the major groove, and inhibits the function of the target DNA by preventing or inhibiting unwinding and/or recognition of the bound sequence. Triplex-forming agents are generally polynucleotides having about 20 to about 40 bases, consisting primarily of G's and T's. Suitable targets for triplex-forming agents are A-G rich regions of sequence, preferably having more than 65% purines on one strand. The most effective triplex-forming agents bind antiparallel to the purine-rich strand, and pair G with G-C pairs, and T with A-T pairs (J. M. Chubb et al., *Tibtech* (1992) 10:132–36).

Figure 1A:
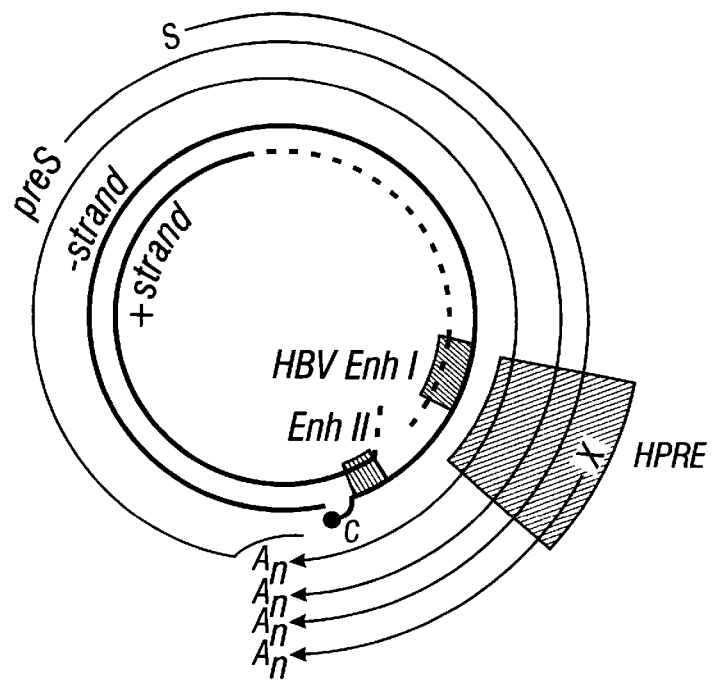

The invention will now be described in further detail.
Isolation of an RNA Export Element, Vectors and Host Cells In a first embodiment, the invention provides an isolated nucleic acid sequence characterized as a cis-acting RNA export element, also referred to herein as WPRE or PRE. WPRE is exemplified by the nucleic acid sequence shown in FIG. 1C and SEQ ID NO:1. WPRE has three sub-elements termed WPREα, WPREβ and WPREγ. Nucleotides 1300–1507 of WHV encompass the minimal WPREα sub-element; 1508–1684 encompass the minimal WREβ sub-element; and 1093–1250 encompass the minimal WPREγ sub-element (FIG. 1C and 6A). The RNA export element of the invention functions with any RNA species, including intronless RNA; spliced RNA; and unspliced RNA, for example.

The term "isolated" as used herein refers to nucleic acids substantially free of other nucleic acids, proteins, lipids, carbohydrates or other materials with which it is naturally associated. Nucleic acid sequences of the invention include DNA and RNA sequences. It is understood that nucleic acid sequences containing all or varying portions of WPRE are included herein, as long as they contain the RNA export activity of at least one of the three sub-elements of WPRE. Preferably, RNA export activity is assayed by measuring the effect of the export element on expression of a gene in cytoplasm. This is readily accomplished by comparing expression of the gene when associated with an export element relative to expression of the gene in the absence of the export element. (See Examples for luciferase or green fluorescent protein (GFP) assay, for example). Nucleic acids of the invention include naturally occurring, synthetic, and intentionally manipulated nucleic. For example, portions of the mRNA sequence which contain the transgene and the RNA export element may be altered due to alternate RNA splicing patterns or the use of alternate promoters for RNA transcription. Moreover, WPRE nucleic acids of the invention include nucleic acids having alterations in the nucleic acid sequence which still contain functional WPRE. Alterations in WPRE nucleic acid include but are not limited to intragenic mutations (e.g., point mutation, nonsense (stop), antisense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. WPRE invention nucleic acid sequences also include antisense sequences. A "functional WPRE nucleic acid" denotes a nucleic acid which contains a functional RNA transport element as described herein.

The WPRE nucleic acid sequences of the invention includes the nucleotide sequence in FIG. 1C (SEQ ID NO:1), as well as nucleic acid sequences complementary to that sequence. A complementary sequence may include an antisense nucleotide. When the sequence is RNA, the deoxyribonucleotides A, G, C, and T of FIG. 1C are replaced by ribonucleotides A, G, C, and U, respectively. Also included in the invention are fragments ("probes") of the above-described WPRE nucleic acid sequences that are at least 15 bases in length, which is sufficient to permit the probe to selectively hybridize to WPRE nucleic acid of FIG. 1C (SEQ ID NO:1). "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated WPRE nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids are considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g. for 10–15 minutes each, in the order listed above, repeating any or all of the steps listed. However, as mentioned above, optimal conditions will vary, depending on the particular hybridization reaction involved, and can be determined empirically.

WPRE nucleic acid sequences of the invention can be obtained by several methods. For example, the DNA can be isolated using hybridization or computer-based techniques which are well known in the art. Such techniques include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library. Since the WPRE nucleic acid sequences of the invention do not appear to "encode" a polypeptide, techniques 1), 3), or 4) above would be most applicable to the present invention.

Screening procedures which rely on nucleic acid hybridization make it possible to isolate any gene sequence from any organism, provided the appropriate probe is available. Oligonucleotide probes, which correspond to apart of the WPRE sequence, can be synthesized chemically.

Nucleic acid constructs containing a transgene and the WPRE of the invention can be transferred in vitro into a suitable host cell. "Host cells" are cells in which a vector can be propagated and its nucleic acid expressed. The term also includes any progeny or graft material, for example, of the subject host cell. It is understood that all progeny may not be identical to the parental cell since there may be mutations that occur during replication. However, such progeny are included when the term "host cell" is used. Methods of stable transfer, meaning that the foreign nucleic acid is continuously maintained in the host, are known in the art.

In the present invention, the WPRE nucleic acid and any other associated nucleic acid sequences may be inserted into a recombinant expression vector. The terms "recombinant expression vector" or "expression vector" refer to a plasmid, virus or other vehicle known in the art that has been manipulated by insertion or incorporation of the desired nucleic acid sequences. Such expression vectors contain a promoter sequence which facilitates the efficient transcription of the inserted transgene and WPRE sequence. The expression vector typically contains an origin of replication, a promoter, as well as specific genes which allow phenotypic selection of the transformed cells.

Methods which are well known to those skilled in the art can be used to construct expression vectors containing the WPRE nucleic acid sequence and other appropriate transcriptional/translational control signals. These methods include in vitro recombinant DNA techniques, synthetic techniques, and in vivo recombination/genetic techniques.

A variety of host-expression vector systems may be utilized to express the transgene associated with the WPRE sequence. These include but are not limited to microorganisms such as bacteria transformed with recombinant bacteriophage DNA, plasmid DNA or cosmid DNA expression vectors containing the WPRE sequence; yeast transformed with recombinant yeast expression vectors containing the WPRE sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the WPRE sequence; insect cell systems infected with recombinant virus expression vectors (e.g., baculovirus) containing the WPRE sequence; or animal cell systems infected with recombinant virus expression vectors (e.g., retroviruses, adenovirus, vaccinia virus) containing the WPRE sequence, or transformed animal cell systems engineered for stable expression.

Depending on the host/vector system utilized, any number of suitable transcription and translation elements, including constitutive and inducible promoters, transcription enhancer elements, transcription terminators, etc. may be used in the expression vector in addition to the RNA transport element of the invention (see e.g. Bitter et al., *Methods in Enzymology* 153:516–544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted transgene/WPRE sequence.

Any of a variety of vectors may be used in the present invention. Exemplary biological vectors include viruses, particularly attenuated and/or replication-deficient viruses. Exemplary chemical vectors include lipid complexes and various formulations comprising the nucleotide sequences of interest. The vectors can contain or be derived from any of a variety of viral constructs, bacterial constructs, or constructs capable of replication in eukaryotic and prokaryotic hosts. Preferably, the construct is capable of replication in both eukaryotic and prokaryotic hosts in order to facilitate efficient production of the DNA of interest for use in the method of the invention. Numerous constructs that can replicate in eukaryotic and prokaryotic hosts are known in the art and are commercially available. The construct may be a stably integrating construct or a stable nonintegrating construct. Examples of such constructs include viral constructs and artificial chromosomes (e.g., human artificial chromosomes). The basic vector components include a promoter operably linked to a nucleotide sequence of interest. Additional components of a basic vector include a polyadenylation signal, a splice signal, and terminal repeat sequences (TR), e.g., TR sequences corresponding to the viral sequence from which a viral vector is derived.

Transformation of target cells may be accomplished by administering a DNA- or RNA-liposome complex formulations. DNA- or RNA- complex formations comprise a mixture of lipids which bind to genetic material (DNA or RNA), providing a hydrophobic coat which allows the genetic material to be delivered into cells. Liposomes which can be used in accordance with the invention include DOPE (dioleyl phosphatidyl ethanol amine), CUDMEDA (N-(5-cholestrum-3-β-ol 3-urethanyl)-N',N'-dimethylethylene diamine) and the like. When the DNA of interest is introduced using a liposome, it is preferable to first determine in vitro the optimal DNA:lipid ratio and the absolute concentrations of DNA and lipid as a function of cell death and transformation efficiency. These values can then be used in or extrapolated for use in in vivo transformation. The in vitro determinations of these values can be readily carried out using techniques which are well known in the art.

Other nonviral vectors may also be used in accordance with the present invention. For example, chemical formulations include DNA or RNA coupled to a carrier molecule (e.g., an antibody or a receptor ligand) which facilitates delivery to host cells for the purpose of altering the biological properties of the host cells. By the term "chemical formulations" is meant modifications of nucleic acids to allow coupling of the nucleic acid compounds to a carrier molecule such as a protein or lipid, or derivative thereof. Exemplary protein carrier molecules include antibodies specific to the cells of a targeted cell or receptor ligands, i.e., molecules capable of interacting with receptors associated with the targeted cell. Alternatively, the DNA of interest may be naked (i.e., not encapsulated), or may be provided as a formulation of DNA and cationic compounds (e.g., dextran sulfate, DEAC-dextran, or poly-L-lysine).

A viral vector may be used in gene therapy according to the present invention. In general, such viral vectors are composed of a viral particle derived from a naturally-occurring virus which has been genetically altered to render the virus replication-defective and to express a recombinant gene of interest. Once the virus delivers its genetic material to a cell, it does not generate additional infectious virus but does introduce exogenous recombinant genes into the cell, preferably into the genome of the cell. Alternatively, the virus containing the DNA of interest is attenuated, i.e. does not cause significant pathology or morbidity in the infected host (i.e., the virus is non-pathogenic or causes only minor disease symptoms). Numerous viral vectors are well known in the art, including, for example, adeno-associated virus (AAV), retrovirus, adenovirus, herpes simplex virus (HSV), cytomegalovirus (CMV), vaccinia and poliovirus vectors. In addition, lentivirus may be used to deliver a DNA of interest to target cells.

Several viral vectors have designed for delivery of nucleotide sequences encoding therapeutic gene products to eukaryotic cells (Cohen-Haguenauer, *Nouvelle Revue Francaise D Hematologie*, 36 Suppl 1: S3–9, 1994). The prototypes for viral mediated gene transfer are the retroviruses (Williams, *Hum. Gene Therap.*, 1(3):229–39, 1990; Merrouche et al., *Hum. Gene Therap.*, 3(3):285–91, 1992; Barba et al, *J. Neurosurg.*, 79(5):729–35, 1993). Retroviral vectors are characterized by their ability to preferentially integrate into the genome of rapidly dividing cells, making them an ideal vector for introducing tumoricidal factors into proliferating neoplastic cells. Adenoviral vectors infect both dividing and nondividing cells with high efficiency. Adenoviral vectors do not integrate into the genome of the target cell (Berkner, *Curr. Topics Microbiol. Immunol.*, 158: 39–66, 1992; Boviatsis et al., *Human Gene Therap.*, 5: 183–191, 1994) and thus provide temporal recombinant gene expression from an extra-chromosomal element for a period of several weeks to a month.

Replication-defective recombinant viruses and plasmid-derived amplicons derived from herpes virus vectors have been developed for gene delivery into cells and tissues (Leib et al., *Bioassays*, 15: 547–54, 1993; Boviatsis et al., *Human Gene Therap.*, 5: 183–191, 1994). Both herpes-derived gene delivery vectors are relatively nonpathogenic to neural tissues and can mediate transgene expression in a substantial number of neurons and other cell types. The recombinant herpes vectors have the distinct advantage that they can enter a latent state in some neuronal cells and thus could potentially mediate stable transgene expression. Adeno-associated virus (AAV) has several desirable characteristics as a vector for gene therapy (Kotin, R. M., *Proc. Natl. Acad Sci. USA*, 87: 2211–5, 1990; Muzyczka, N., *Curr. Topics Microbiol. Immunol.*, 158: 97–129, 1992). AAV is nonpathogenic in both humans and animals and has a broad host range including human, primate, canine and murine. Its ability to infect and integrate into nondividing cells with high frequency makes it a desirable vector for transfecting quiescent lymphoid or myeloid cells. AAV integration is stable; AAV remained stably integrated in the genome of transformed cells through 150 passages.

Where a viral vector is used to accomplish transformation of a target cell, the viral vector is preferably derived from a replication-deficient virus. When a replication-deficient virus is used as the viral vector, infective virus particles containing either DNA or RNA corresponding to the desired therapeutic gene product can be produced by introducing the viral construct into a recombinant cell line which provides the missing components essential for viral replication in trans. Preferably, transformation of the recombinant cell line with the recombinant viral vector will not result in production of replication-competent viruses (e.g., by homologous recombination of the viral sequences of the recombinant cell line into the introduced viral vector).

Methods for production of replication-deficient viral particles containing a nucleotide sequence of interest are well known in the art and are described in, for example, Rosenfeld et al., *Science* 252:431–434, 1991 and Rosenfeld et al., *Cell* 68:143–155, 1992 (adenovirus); U.S. Pat. No. 5,139,941 (adeno-associated virus); U.S. Pat. No. 4,861,719 (retrovirus); and U.S. Pat. No. 5,356,806 (vaccinia virus).

The transformation vector is composed of (in the case of a nonviral vector) or derived from (in the case of recombinant viral vectors) a DNA construct. Preferably, the DNA construct contains a promoter to facilitate expression of the DNA of interest within the target cell. Preferably the promoter is a strong, eukaryotic promoter. Exemplary eukaryotic promoters include promoters from cytomegalovirus (CMV), mouse mammary tumor virus (MMTV), Rous sarcoma virus (RSV), adenovirus, herpes simplex virus (HSV) (e.g., HSV thymidine kinase promoter), and SV40. More specifically, exemplary promoters include the Ad 2 major late promoter (Wong et al. *J. Virol.* 60(1):149–56, 1986), the promoter from the immediate early gene of human CMV (Boshart et al., *Cell* 41:521–530, 1985) and the promoter from the long terminal repeat (LTR) of RSV (Gorman et al., *Proc. Natl. Acad. Sci. USA* 70:6777–6781, 1982). Of these promoters, the CMV and Ad 2 major late promoters are especially preferred.

Other components of the DNA construct include a marker (s) (e.g., an antibiotic resistance gene (such as an ampicillin resistance gene, β-galactosidase or green fluorescent protein (GFP)) to aid in selection of cells containing the construct, an origin of replication for stable replication of the construct in a bacterial cell (preferably, a high copy number origin of replication), a nuclear localization signal, or other elements which facilitate production of the DNA construct including the WPRE, the protein encoded thereby, or both.

For eukaryotic expression, the construct should contain at a minimum a eukaryotic promoter operably linked to the nucleic acid of interest, which is in turn operably linked to a polyadenylation sequence. The polyadenylation signal sequence may be selected from any of a variety of polyadenylation signal sequences known in the art. Preferably, the polyadenylation signal sequences are the polyadenylation signal sequences of the SV40 late and/or early genes.

The nucleic acid of interest can be inserted into a construct so that the protein is expressed as a fusion protein associated with WPRE. For example, the protein can be a portion of a fusion protein having β-galactosidase or a portion thereof at the N-terminus and a therapeutic protein at the C-terminus. Alternatively, the protein (or a portion thereof) can be fused to green fluorescent protein (or a portion thereof). Methods for production of such fusion proteins are well known in the art (see, for example, Sambrook et al. *Molecular Cloning: A Laboratory Manual*, 2nd Ed., 1989, Cold Spring Harbor Laboratory Press, Cold Spring Harbor, NY; Kain et al. 1995 *Biotechniques* 19:650–655; and Clontech Laboratories, Inc., *Technical Service Protocol #PT*2040-1, Version #PR64559, each of which are hereby incorporated by reference with respect to methods and compositions for production and expression of fusion proteins). Production of a fusion protein can facilitate monitoring of therapy, e.g., through detection of the fusion protein from a sample of peripheral blood.

It may also be desirable to produce altered forms of the proteins that are, for example, protease resistant or have enhanced activity relative to the wild-type protein. Further, where the therapeutic protein is a hormone, it may be desirable to alter the protein's ability to form dimers or multimeric complexes.

The DNA construct containing the nucleic acid of interest can also be designed so as to provide for site-specific integration into the genome of the target cell. Methods and compositions for preparation of such site-specific constructs are described in, for example, U.S. Pat. No. 5,292,662, incorporated herein by reference with respect to the construction and use of such site-specific insertion vectors. Techniques for production of nucleic acid constructs for expression of exogenous DNA or RNA sequences in a host are known in the art (see, for example, Kormal et al., *Proc. Natl. Acad Sci. USA*, 84:2150–2154, 1987; and Sambrook et al., supra, each of which are hereby incorporated by reference with respect to methods and compositions for eukaryotic expression of a DNA of interest).

The invention RNA export element or WPRE may be used in the same or different species from which it is derived or in which it naturally functions. A natural posttranscriptional regulatory element comprises a DNA sequence which in its native environment is generally downstream from a structural gene, e.g., a transgene. The invention RNA export element is cis-acting and desirably is located within the RNA transgene gene, as long as the element is in operable linkage within the transgene mRNA. The RNA export element can be located upstream or downstream in relation to the transgene as long as it is transcribed within the transgene mRNA, however, preferably, it is located downstream to avoid disruption of translation.

The RNA export element of the invention can be utilized with a variety of transgenes, including transgenes that are naturally found under control of the element (homologous) as well as transgenes not naturally associated with the element region (heterologous).

Enhanced gene expression in cells such as mammalian or plant cells, is useful in obtaining high levels of endogenous gene expression as well as high levels of exogenous gene expression. The term "endogenous" as used herein refers to a gene normally found in the wild-type host, while the term "exogenous" refers to a gene not normally found in the wild-type host.

The invention WPRE is operably linked with a heterologous nucleic acid or transgene which includes a transcription initiation domain. The term "transcription initiation domain" refers to a promoter having at least an RNA polymerase binding site and an mRNA initiation site. A promoter, in turn, is operably associated with the transgene, which, when including an open reading frame (ORF), encodes a protein, and typically also includes the 5' and 3' untranslated sequences. Such open reading frames, or RNA encoding sequences include natural open reading frames encoding protein products; cDNA sequences derived from mRNA; synthetic DNA; protein encoding sequences derived from exons of the natural gene (e.g., open reading frame produced by exon ligation); and/or combinations of the above. The appropriate transcription termination and polyadenylation sequences are also included. Preferably, the WPRE is present at the 3' end of the transgene upstream of the transcription termination and polyadenylation sequences. It is understood however that it is possible to orient WPRE at the 5' end of the transgene. In either case, the WPRE must be in the sense orientation.

Heterologous nucleic acids, the level of expression of which may be increased according the present invention, include, for example, sequences from the natural genes (plant, animal, bacterial, viral, fungal) which encode primary RNA products; synthetic DNA sequences which encode a specific RNA or protein product; DNA sequences modified by mutagenesis, for example site specific mutagenesis; chimeras of any of the above (to produce fusion proteins); and DNA sequences encoding complementary RNA molecules (antisense); triplex agents (triple helix), ribozymes, and combinations and/or fragments of the above. Antisense, triplex agents and ribozymes do not "encode" polypeptides, however, their cytoplasmic concentration can be elevated using the invention WPRE as described herein.

Both sense and antisense nucleic acids can be used in the construct employed in the invention. For example, a sense polynucleotide sequence (the DNA coding strand) encoding a polypeptide can be introduced into a cell to increase expression of a "normal" gene. When it is desirable to use nucleic acid sequences that interfere with expression at the translational level, antisense nucleic acids, ribozymes, or triplex agents can be employed to block transcription or translation of a specific mRNA, either by masking that mRNA with an antisense nucleic acid or triplex agent, or by cleaving it with a ribozyme. Alternatively, one may employ a reagent that mimics the action or effect of a gene product or blocks the action of the gene. Therefore, when it is desirable to achieve increased concentration of cytoplasmic antisense nucleic acid, utilizing the WPRE of the invention provides a means to achieve increased levels of the antisense.

The use of antisense methods to inhibit the in vitro translation of genes is well known in the art (see, e.g., Marcus-Sakura, *Anal. Biochem.*, 172:289, 1988). Antisense nucleic acids are molecules containing DNA nucleotides, RNA nucleotides, or modifications that increase the stability of the molecule, such as 2'-O-alkyl substituted nucleotides or combinations thereof that are complementary to, or that hybridize to, at least a portion of a specific nucleic acid molecule, such as an RNA molecule (e.g., an mRNA molecule) (see, e.g., Weintraub, *Scientific American*, 262:40, 1990). The antisense nucleic acids hybridize to corresponding nucleic acids, such as mRNAs, to form a double-stranded molecule, which interferes with translation of the mRNA, as the cell will not translate a double-stranded mRNA. Antisense nucleic acids used in the invention are typically at least 10–12 nucleotides in length, for example, at least 15, 20, 25, 50, 75, or 100 nucleotides in length. The antisense nucleic acid can also be as long as the target nucleic acid with which it is intended to form an inhibitory duplex. As is described below, antisense nucleic acids can be introduced into cells as antisense oligonucleotide, or can be produced in a cell in which a nucleic acid encoding the antisense nucleic acid has been introduced by, for example, using gene therapy methods.

Phosphodiester-linked antisense polynucleotides are particularly susceptible to the action of nucleases in serum or inside cells, and therefore in a preferred embodiment the antisense polynucleotides of the present invention are phosphorothioate or methyl phosphonate-linked analogues, which have been shown to be nuclease-resistant. One of ordinary skill in this art will be able to select other linkages for use in the invention. These modifications also may be designed to improve the cellular uptake and stability of the polynucleotides.

Examples of heterologous nucleic acids encoding proteins that can be produced at increased levels utilizing the present invention in cells include, but are not limited to a growth factors, cytokines, hormones, neurotrophic factors, toxins and immunoregulatory agents.

Nucleic acids encoding therapeutic agents including immunomodulators and other biological response modifiers are advantageously employed in the present invention in connection with immunotherapy. The term "biological response modifiers" encompasses substances which are involved in modifying the immune response in such manner as to enhance the destruction of tumor, for example. Examples of immune response modifiers include such compounds as lymphokines. Lymphokines include tumor necrosis factor, the interleukins, lymphotoxin, macrophage activating factor, migration inhibition factor, colony stimulating factor, and interferon. Included in this category are immunopotentiating agents including nucleic acids encoding a number of cytokines classified as "interleukins". These include, for example, interleukins 1 through 15. Also included in this category, although not necessarily functioning in the same manner are interferons, and in particular gamma interferon (γ-IFN), tumor necrosis factor (TNF) and granulocyte-macrophage-colony stimulating factor (GM-CSF). Nucleic acids encoding growth factors, toxic peptides, ligands, receptors, suicide factors (e.g., TK), coagulation cascade factors (e.g., Factor VIII, Factor V), viral polypeptides, hormones, neurotransmitters, enzymes, or other physiologically important proteins can also be introduced into specific cells of a plant or a subject such as a mammal or more specifically a human.

Examples of proteins that can be produced at increased levels utilizing the present invention in plant cells include, but are not limited to, nutritionally important proteins; growth promoting factors; proteins for early flowering in plants; proteins giving protection to the plant under certain environmental conditions, e.g., proteins conferring resistance to metals or other toxic substances, such as herbicides or pesticides; stress related proteins which confer tolerance to temperature extremes; proteins conferring resistance to fungi, bacteria, viruses, insects and nematodes; proteins of specific commercial value, e.g., enzymes involved in metabolic pathways, such as EPSP synthase.

Method for Enhancing Gene Expression

The present invention provides a method for enhancing gene expression or increasing the cytoplasmic concentration of a nucleic acid in a cell comprising operably associating the cis-acting RNA export element of the invention to a heterologous nucleic acid sequence, wherein the cis-acting RNA export element enhances transport of the resulting mRNA transcript, from the nucleus to the cytoplasm thereby resulting in enhanced expression. The RNA export element, or WPRE, is preferably associated with a transgene and present in a vector or construct as described above. Heterologous nucleic acid sequences including antisense and triplex nucleic acids, as well as nucleic acids encoding polypeptides such as growth factors, coagulation cascade factors, hormones, cytokines and other polypeptides as described above, are exemplary nucleic acid sequences that can be operably associated with the WPRE of the invention for enhancing gene expression or cytoplasmic concentrations of a particular nucleic acid.

Description of constructs used in the method for mammalian cells or plant cells, for example, are described in detail above.

Administration of RNA Export Element-Containing Constructs

Formulation of a preparation for administration of the RNA export element containing constructs will depend upon several factors such as the cell targeted for gene transfer and whether a biological or nonbiological vector is employed. The vector solution can also contain therapeutic agents (e.g., nerve growth factors, anti-inflammatory agents, antibiotic agents) in addition to the DNA of interest, as well as agents to adjust, for example, the pH, osmolarity, and/or viscosity of the vector solution. The preparation can additionally contain agents that facilitate entry of the constructs into cells. Such agents include lipofectin, permeability-enhancing agents (e.g., detergents), and other transformation-enhancing agents. When a viral vector is employed, the preparation can also include a co-infecting virus to facilitate infection and transformation. When the nucleic acid of interest is administered in a recombinant viral vector, e.g. an AAV vector, the vector solution is preferably normal saline.

The amount of construct and/or number of viral particles administered will vary greatly according to a number of factors including the susceptibility of the target cells to transformation, subject-dependent variables such as age, weight, sensitivity or responsiveness to therapy, the levels of protein expression desired, and the condition to be treated. For example, when a recombinant AAV vector is used, the total delivered viral dosage can be in the range of 1 virus per 5 target cells, preferably 1 virus per 10 target cells, more preferably 1 virus per 20 target cells or less. Generally, the amount of construct nucleic acid for transformation of human target cells can be extrapolated from the amounts of nucleic acid effective for gene therapy in an animal model.

The amount of construct nucleic acid and/or viral particles necessary to accomplish transformation of the target cells will decrease with an increase in the efficiency of the transformation method used. In general, the amount of construct nucleic acid and/or the number of infectious viral particles employed is an amount effective to infect the targeted cells or structure, transform a sufficient number of cells, and provide for expression of desired or therapeutic levels of the protein of interest or other gene product. Where transformation is transient (e.g., the DNA of interest is maintained for some period as an extrachromosomal element), the time period over which expression is desired may also be taken into consideration. The desired number of copies (e.g., copy number) of the DNA of interest in the cell may additionally be taken into account in determining the amount of construct nucleic acid and/or number of viral particles to be delivered to the subject, and such may be adjusted as desired to, for example, achieve varying levels of gene product expression.

Transformation can be accomplished such that expression of the gene product of interest is either transient, inducible, or stable. For example, when the DNA of interest is present in the transformed cell as an extrachromosomal element (e.g., as with AAV vectors), expression of the gene product is generally transient. Inducible expression can be employed so that expression of the gene product occurs only in the presence of a signal that is specific to a certain type of cell (e.g., is only expressed in HIV-infected myeloid cells or a specific type of myeloid or lymphoid cell due to the presence of a cell-specific or tissue-specific transcription factor or WPRE binding protein in the transformed cell). Alternatively, gene product can be induced an extracellular factor that can be introduced at the same time the transforming vector solution is introduced. Stable expression of the gene product can be achieved by, for example, introduction of the DNA of interest in a vector to provide for stable genomic integration into the target cell and expression of the gene product from the DNA of interest by means of a constitutive promoter.

Where expression of the gene product of interest is transient, expression can be maintained in the target cell for a period ranging from several days to several months or years, e.g., for 6 months to 1 year, for 4 months to 6 months, for 2 weeks to 8 weeks, or for as little as one week or a few days (e.g., 3 to 5 days, or 1 to 3 days). Transient expression of the gene product of interest may be desirable when the subject is being exposed to a therapeutic regimen for the first time (e.g., when it is desirable to monitor the responsiveness and/or sensitivity of the subject), or where expression is desired only over a specific period (e.g., for a period alter transplantation without permanent expression, or for a period during a specific stage of development). The period of transient expression can be adjusted by, for example, adjusting the transformation protocol to achieve a desired number of transformed cells or, where a viral vector is used, by adjusting aspects of the vector associated with maintenance in a cell (e.g., replication functions or other functions associated with vector stability and/or copy number).

The actual amounts of DNA construct and/or number of infectious viral particles required can be readily determined based upon such factors as the levels of protein expression achieved in cell lines in vitro, and the susceptibility of the target cells to transformation.

Administration of constructs or vectors containing the WPRE of the invention and a heterologous nucleic acid, either as a naked, synthetic polynucleotide or as part of an expression vector, can be effected via any common route (oral, nasal, buccal, rectal, vaginal, or topical), or by subcutaneous, intramuscular, intraperitoneal, or intravenous injection. Pharmaceutical compositions of the present invention, however, are advantageously administered in the form of injectable compositions. A typical composition for such purpose comprises a pharmaceutically acceptable solvent or diluent and other suitable, physiologic compounds. For instance, the composition may contain polynucleotide and about 10 mg of human serum albumin per milliliter of a phosphate buffer containing NaCl.

As much as 700 milligrams of antisense polynucleotide has been administered intravenously to a patient over a course of 10 days (i.e., 0.05 mg/kg/hour) without signs of toxicity. Sterling, "Systemic Antisense Treatment Reported," *Genetic Engineering News* 12: 1, 28, 1992.

Other pharmaceutically acceptable excipients include non-aqueous or aqueous solutions and non-toxic compositions including salts, preservatives, buffers and the like. Examples of non-aqueous solutions are propylene glycol, polyethylene glycol, vegetable oil and injectable organic esters such as ethyloleate. Aqueous solutions include water, alcoholic/aqueous solutions, saline solutions, parenteral vehicles such as sodium chloride, Ringer's dextrose, etc. Intravenous vehicles include fluid and nutrient replenishers. Preservatives include antimicrobial, anti-oxidants, chelating agents and inert gases. The pH and exact concentration of the various components the pharmaceutical composition are adjusted according to routine skills in the art. A preferred pharmaceutical composition for topical administration is a dermal cream or transdermal patch.

Expression vectors or naked WPRE/heterologous nucleic acid constructs may be administered by injection as an oily suspension. Suitable lipophilic solvents or vehicles include fatty oils, such as sesame oil, or synthetic fatty acid esters, such as ethyl oleate or triglycerides. Moreover, antisense polynucleotides or vectors may be combined with a lipophilic carrier such as any one of a number of sterols including cholesterol, cholate and deoxycholic acid. A preferred sterol is cholesterol. Aqueous injection suspensions may contain substances which increase the viscosity of the suspension include, for example, sodium carboxymethyl cellulose, sorbitol, and/or dextran. Optionally, the suspension also contains stabilizers.

An alternative formulation for the administration of invention constructs containing WPRE containing nucleic acid sequences involves liposomes. Liposome encapsulation provides an alternative formulation for the administration expression vectors. Liposomes are microscopic vesicles that consist of one or more lipid bilayers surrounding aqueous compartments. See, generally, Bakker-Woudenberg et al., *Eur. J Clin. Microbiol. Infect. Dis.* 12 (Suppl. 1): S61, 1993, and Kim, *Drugs* 46: 618, 1993. Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s). See, for example. Machy et al., LIPOSOMES IN CELL BIOLOGY AND PHARMACOLOGY (John Libbey 1987), and Ostro et al., *American J. Hosp. Pharm.* 46: 1576, 1989. Moreover, it is possible to control the therapeutic availability of the encapsulated agent by varying liposome size, the number of bilayers, lipid composition, as well as the charge and surface characteristics of the liposomes.

Liposomes adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents. Scherphofet al., *Ann. N.Y. Acad. Sci.* 446: 368, 1985.

After intravenous administration, conventional liposomes are preferentially phagocytosed into the reticuloendothelial system. However, the reticuloendothelial system can be circumvented by several methods including saturation with large doses of liposome particles, or selective macrophage inactivation by pharmacological means. Claassen et al., *Biochim. Biophys. Acta* 802: 428, 1984. In addition, incorporation of glycolipid- or polyethylene glycol-derivatised phospholipids into liposome membranes has been shown to result in a significantly reduced uptake by the reticuloendothelial system. Allen et al., *Biochim. Biophys. Acta* 1068: 133, 1991; Allen et al., *Biochim. Biohys. Acta* 1150: 9, 1993 These Stealth® liposomes have an increased circulation time and an improved targeting to tumors in animals. Woodle et al., *Proc. Amer. Assoc. Cancer Res.* 33: 2672, 1992. Human clinical trials are in progress, including Phase III clinical trials against Kaposi's sarcoma. Gregoriadis et al., *Drugs* 45: 15, 1993.

Expression vectors can be encapsulated within liposomes using standard techniques. A variety of different liposome compositions and methods for synthesis are known to those of skill in the art. See, for example, U.S. Pat. No. 4,844,904, U.S. Pat. No. 5,000,959, U.S. Pat. No. 4,863,740, and U.S. Pat. No. 4,975,282, all of which are hereby incorporated by reference.

Liposomes can be prepared for targeting to particular cells or organs by varying phospholipid composition or by inserting receptors or ligands into the liposomes. For instance, antibodies specific to tumor associated antigens may be incorporated into liposomes, together with antisense polynucleotides or expression vectors, to target the liposome more effectively to the tumor cells. See, for example, Zelphati et al., *Antisense Research and Development* 3: 323–338, 1993, describing the use "immunoliposomes" containing invention constructs for human therapy.

In general, the dosage of liposome-encapsulated antisense polynucleotides and vectors will vary depending upon such factors as the patient's age, weight, height, sex, general medical condition and previous medical history. Dose ranges for particular formulations can be determined by using a suitable animal model.

When the WPRE-containing vectors of the invention are to be utilized in plant cells, such constructs can be introduced using Ti plasmids, root-inducing (Ri) plasmids, and plant virus vectors. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9, and Horsch, et al., *Science,* 227:1229, 1985, both incorporated herein by reference.

One of skill in the art will be able to select an appropriate vector for introducing the WPRE containing vectors of the invention in a relatively intact state to plant cells. Thus, any vector which will produce a plant carrying the introduced vector should be sufficient. Even a naked piece of DNA would be expected to be able to confer the properties of this invention, though at low efficiency. Selection of the vector, or whether to use a vector, is typically guided by the method of transformation selected.

For example, WPRE containing constructs can be introduced into a plant cell utilizing *Agrobacterium tumefaciens* containing the Ti plasmid. When using an *A. tumefaciens* culture as a transformation vehicle, it is most advantageous to use a non-oncogenic strain of the Agrobacterium as the vector carrier so that normal non-oncogenic differentiation of the transformed tissues is possible. It is also preferred that the Agrobacterium harbor a binary Ti plasmid system. Such a binary system comprises 1) a first Ti plasmid having a virulence region essential for the introduction of transfer DNA (T-DNA) into plants, and 2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells (De Framond, *Biotechnology,* 1:262, 1983; Hoekema, et al., *Nature,* 303:179, 1983). Such a binary system is preferred because it does not require integration into Ti plasmid in Agrobacterium.

Methods involving the use of Agrobacterium include, but are not limited to: 1) co-cultivation of Agrobacterium with cultured isolated protoplasts; 2) transformation of plant cells or tissues with Agrobacterium; or 3) transformation of seeds, apices or meristems with Agrobacterium.

In addition, gene transfer in plants can be accomplished by in situ transformation by Agrobacterium, as described by Bechtold, et al., (*C.R. Acad Sci. Paris,* 316:1194, 1993). This approach is based on the vacuum infiltration of a suspension of Agrobacterium cells.

The preferred method of introducing nucleic acid into plant cells is to infect such plant cells, an explant, a meristem or a seed, with transformed *Agrobacterium tumefaciens* as described above. Under appropriate conditions known in the art, the transformed plant cells are grown to form shoots, roots, and develop further into plants.

Alternatively, the WPRE-containing constructs described herein can be introduced into a plant cell by contacting the plant cell using mechanical or chemical means. For example, nucleic acid can be mechanically transferred by direct microinjection into plant cells utilizing micropipettes. Moreover, the nucleic acid may be transferred into plant cells using polyethylene glycol which forms a precipitation complex with genetic material that is taken up by the cell.

The nucleic acid can also be introduced into plant cells by electroporation (Fromm, et al, *Proc. Natl. Acad Sci., U.S.A.,* 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize plant membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing nucleic acid into a plant cell is high velocity ballistic penetration by small particles with the nucleic acid to be introduced contained either within the matrix of small beads or particles, or on the surface thereof (Klein, et al., *Nature* 327:70, 1987). Although, typically only a single introduction of a new nucleic acid sequence is required, this method particularly provides for multiple introductions.

Cauliflower mosaic virus (CaMV) may also be used as a vector for introducing heterologous nucleic acid into plant cells (U.S. Pat. No. 4,407,956). The CaMV viral DNA genome is inserted into a parent bacterial plasmid creating a recombinant DNA molecule which can be propagated in bacteria. After cloning, the recombinant plasmid may be re-cloned and further modified by introduction of the desired nucleic acid sequence. The modified viral portion of the recombinant plasmid is then excised from the parent bacterial plasmid, and used to inoculate the plant cells or plants.

Screen for Identification of RNA Export Element Binding Proteins or Agents which Modulate RNA Export Element Activity The invention also provides a method for identifying a cellular protein which binds to the invention cis-acting RNA export element comprising incubating the export element operably associated with a heterologous DNA or mRNA with a suspected binding protein; separating the resulting complex of export element and binding protein from unbound export element and isolating the protein. The method includes screening for agents which modulate RNA export element activity. The term "modulate" refers to inhibition or enhancement of RNA export element activity.

The method includes incubating components comprising the suspected protein or agent, e.g., binding agent and a nucleic acid sequence containing the WPRE or subelements thereof as described herein (e.g., WPREα under conditions sufficient to allow the components to form a complex and detecting the presence of agent or protein bound by size separation, physical separation, or other standard methods. Agents that bind to the WPRE of the invention include peptides, peptidomimetics, polypeptides, chemical compounds, small molecules and biological agents, for example. One of skill in the art could screen for binding of an agent to the WPRE or an effect on the WPRE by assays described herein, for example, expression of a reporter gene such as luciferase or GFP to determine if a protein or agent is a WPRE binding protein or agent.

Incubation includes conditions which allow contact between the protein or agent and WPRE containing nucleic acid sequence. Contacting includes in solution and in solid phase. The test agent may optionally be a combinatorial library that permits screening a plurality of agents. Agents identified in the method of the invention can be further evaluated, detected, cloned, sequenced, and the like, either in solution or after binding to a solid support, by any method usually applied to the detection of a small molecule or a specific nucleic acid sequence. Nucleic acid sequences can be analyzed by commonly used techniques such as PCR, oligomer restriction (Saild, et al., *Bio/Technology,* 3:1008–1012, 1985), allele-specific oligonucleotide (ASO) probe analysis (Conner, et al., *Proc. Natl. Acad. Sci. USA,* 80:278, 1983), oligonucleotide ligation assays (OLAs) (Landegren, et al., *Science,* 241:1077, 1988), and the like. Molecular techniques for nucleic acid analysis have been reviewed (Landegren, et al., *Science,* 242:229–237, 1988).

To determine if an agent or protein can functionally complex with the WPRE, the agent or protein is incubated and any complex formed between WPRE and the agent or WPRE and a protein is separated from unbound WPRE. The agent or protein can then be isolated from the WPRE complex.

Also included in the screening method of the invention are combinatorial chemistry methods for identifying chemical compounds that bind to WPRE. Agents that bind to WPRE can be assayed in standard labeling assays.

Test agents or proteins can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the test agent, or will be able to ascertain such, using routine experimentation.

It should be understood that all of the WPRE of the invention or individual sub-elements (i.e., PREα, PREβ, or PREγ) can be used in the method of the invention. Thus, binding proteins or binding agents can be identified that bind to specific subelements of the WPRE if desired.

Screen for Identification of RNA Export Elements

In yet another embodiment, the invention provides a method for identifying a cis-acting RNA export element including measuring the effect of a putative export element on the expression of a heterologous nucleic acid sequence in the cytoplasm; selecting those elements which provide greater levels of expression relative to the level of expression attainable in the absence of said export element. The method optionally includes operably associating a cis-acting RNA export element of the invention to a heterologous nucleic acid sequence and measuring expression of the nucleic acid sequence in the presence and absence of the export element and comparing expression of the heterologous nucleic acid sequence in the presence and absence of the export element of the invention with expression of the heterologous nucleic acid sequence in the presence and absence of the putative export element, wherein increased expression of the nucleic acid sequence operably associated with the putative cis-acting RNA export as compared with expression of the nucleic acid sequence in the absence of the export element of the invention, is indicative of the presence of a cis-acting RNA export element.

One of skill in the art can use assays as described herein to identify putative RNA export elements. For example, the heterologous nucleic acid linked with the WPRE of the invention and the putative RNA export element is typically a reporter or indicator polypeptide. A "reporter" or "indicator" polypeptide refers to a polypeptide that allows one of skill in the art to measure in some way (e.g., by spectrophotometric means; by radiographic means; by fluorescence) the level of expression of a gene encoding that indicator or reporter polypeptide. Exemplary indicator polypeptides used in similar assays in the Examples herein include luciferase and green fluorescent protein (GFP).

The above disclosure generally describes the present invention. A more complete understanding can be obtained by reference to the following specific examples which are provided herein for purposes of illustration only and are not intended to limit the scope of the invention.

EXAMPLE 1

Material and Methods

Construction of Reporter Plasmids. The pDM138 vector system has been previously described Hope, 1992 ref. To construct the pDM138 reporter derivatives, 32 base oligos were synthesized and used to PCR amplify the fragment of interest from the DNA template. The oligos consisted of 5' sequence of GCGGGATCCATCGAT (SEQ ID NO:2) followed by 20 bases of the HPRE or WPRE sequence. The WPRE fragments were amplified from the viral DNA template of WHV accession J04514. The amplified fragments were purified on a 2% agarose gel, digested with Cla I and subsequently ligated into the Cla I site of pDM138. The pGL3 vector (Promega) was digested with Sma and the Cla I-digested WPRE and HPRE fragments were Klenow treated and ligated into the pGL3 vector. The CMV-Surface expression construct was synthesized by amplifying nucleotides 135 to 1685 from D00329. The amplified fragment was digested with SacI and Bgl II and ligated into a SacI - BglIII digested CMV expression construct The HPRE was then removed from this construct by digesting with EcoRV. The vector was religated to yield the HPRE Surface expression vector. The HPRE(963–1684) and WPRE(1093–1684) fragments were then ligated into the ClaI site. The mCC1 mutant was also synthesized via PCR. The HPREα/WPREβ and WPREγα/HPREβ constructs were constructed by PCR mutagenesis. Briefly, a mutant WPRE was synthesized with a single nucleotide change at nucleotide 1533, which produces a Bam HI site (WPrE BamHI) and cloned into the Cla I site of pDM138. The mutant and the WPRE activities were identical (data not shown). p138HPRE(963–1684) and p138WPRE BamHI were digested with Cla I and Bam HI. The 5' and 3' fragments from both digestions were gel isolated. The fragments were then religated the corresponding fragment into the pDM138 vector.

Tissue Culture and Transfections. CV1, CEF and HEPG2 cells were maintained in 5% CO2, with 10% FCS, Dulbeccos Modified Eagles Media. LMH cells (Kawaguchi et al., 1987) were grown in a 1:1 mix of DMEM and Ham's F12 media supplemented with 10% FCS in 5%$CO_2$. All of the cells were grown in 10 cm plates. Before the cells were transfected, the media was removed and the DNA-$CaPO_4$ mix was added directly to the naked cells. After 10 min, 5 mL of media was placed back onto the cells. Media was changed 16 hours after transfection. The cells were harvested 36–48 hours later. For the CAT assays, CV1, CEF, LMH and HepG2 cells were transfected in triplicate with 2 ug reporter plasmid, 1 ug pCH110, and 7 ug pUC 118 via the $CaPO_4$ method. For the luciferase assays, CV1 cells were transfected when the 10 cm dish was approximately 30% confluent. The cells were transfected in triplicate with 2 ug of the luciferase reporter, 1 ug of pCH110, and 7 ug of pUC118. The luciferase activity was determined by standard methods. To assay for Surface expression, CV1 cells were transfected in duplicate with 25 ug Surface expression vector and 5 ug CMV Secreted Alkaline Phosphotase (SEAP). HepG2 cells were transfected when the cells were approximately 70% confluent. The media was changed approximately 16 hours after transfection. The spent media was harvested 48 hours later.

CAT Assays. CV-1 cells were lifted using phosphate buffer saline (PBS) and 5 mM EDTA and resuspended in 150 ul of Reporter Lysis Buffer (Promega). The lysates were spun briefly to pellet insoluble cell debris. An aliquot of each lysate was assayed for b-galactosidase activity which was then used to normalize each lysate for transfection efficiency. The normalized lysates, equalized with Reporter Lysis Buffer, were incubated at 37 C. for 30 minutes to several hours with 1.5 nCi/ul [$^{14}C$]chloramphenicol (50–60 mCi/mmole) and 1 mM acetyl coenzyme A in 50 ul volumes. Substrate and products were resolved by thin layer chromatography and quantitated by a phosphorimager (Molecular Dynamics).

Surface Expression Radioimmunoassay. The spent media from duplicate transfections was assayed for the presence of Surface antigen with the Ausria II kit (Abbott Laboratories) and quantitated in a gamma counter. As an indicator of transfection efficiencies, the media was also assayed for the presence of SEAP.

EXAMPLE 2

To assay for export activity, the well characterized pDM138 system was utilized.

Figure 1B:
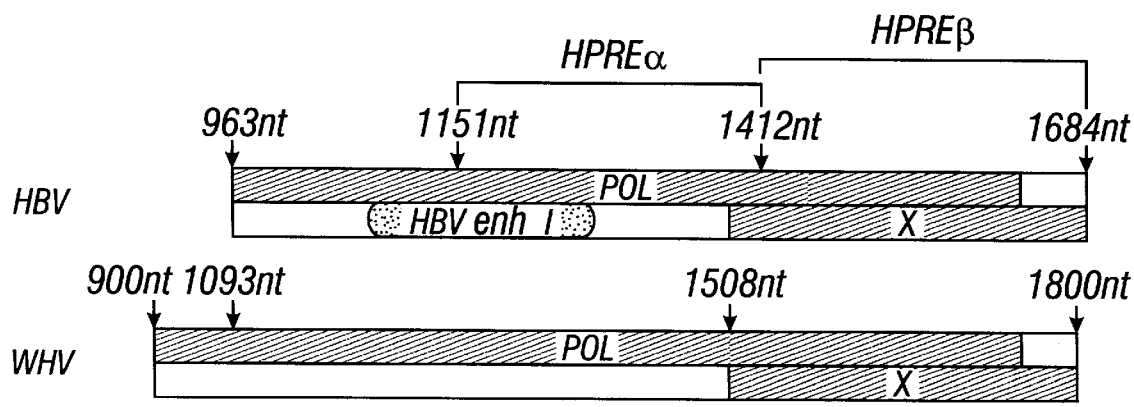

Briefly, the pDM138 reporter was derived from the second intron of HIV-1, into which the chloramphenicol acetyltransferase (CAT) gene was inserted. When the pDM138 reporter is transiently transfected, RNAs transcribed from the reporter are either spliced, which removes the CAT coding region, or exported from the nucleus unspliced. The appearance of unspliced RNAs in the cytoplasm is dependent upon the presence of an RNA export element. When the unspliced RNAs are exported from the nucleus CAT is translated and can be accurately quantitated. The background activity of the empty pDM138 vector is reproducible within a cell line but varies between cell lines. Hence, fold inductions cannot be compared between cell lines. Instead, the activity of an element will be reported as a percentage of the HPRE or WPRE activity. For this study, the nucleotide numbers of accession number J04514 (WHV) and D00329 (HBV) were used. Consequently, homologous nucleotides are offset by 130 bases. For example, WPRE nucleotide 1093 is homologous to HBV nucleotide 963 (FIG. 1B). The schematic in each figure is drawn to scale and the homologous nucleotides of WPRE and HPRE are aligned.

Figure 2A:
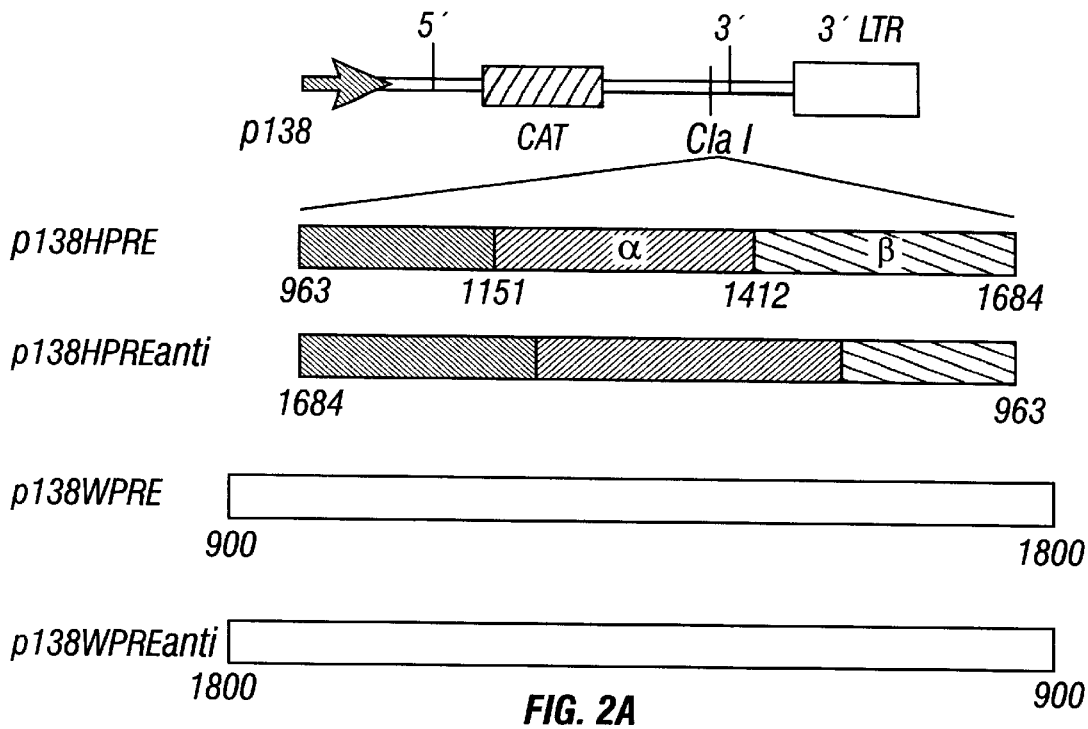
FIGS. 2A–2C show tissue type differences of HPRE and WPRE.

To address whether the WHV region homologous to the HPRE encoded a post transcriptional regulatory element, WHV nucleotides 900–1800 were inserted into the pDM138 vector system in the sense and antisense orientations (FIG. 2A). To avoid the strong transcriptional effects of HBV enhancer I, the WHV and HBV constructs were transiently transfected into CV1 cells and Chicken Embryo Fibroblasts (CEFs). The results are presented in FIG. 2B. In CV1 cells, the p138WPRE(900–1800) reporter was approximately three times as active as the homologous p138HPRE (963–1684). The observed activities were orientation dependent since both antisense controls were below the empty pDM138 background control. Similar results were observed in CEFs, in which p138WPRE(900–1800) was approximately two times as active as p138HPRE(963–1684).

Figure 2C:
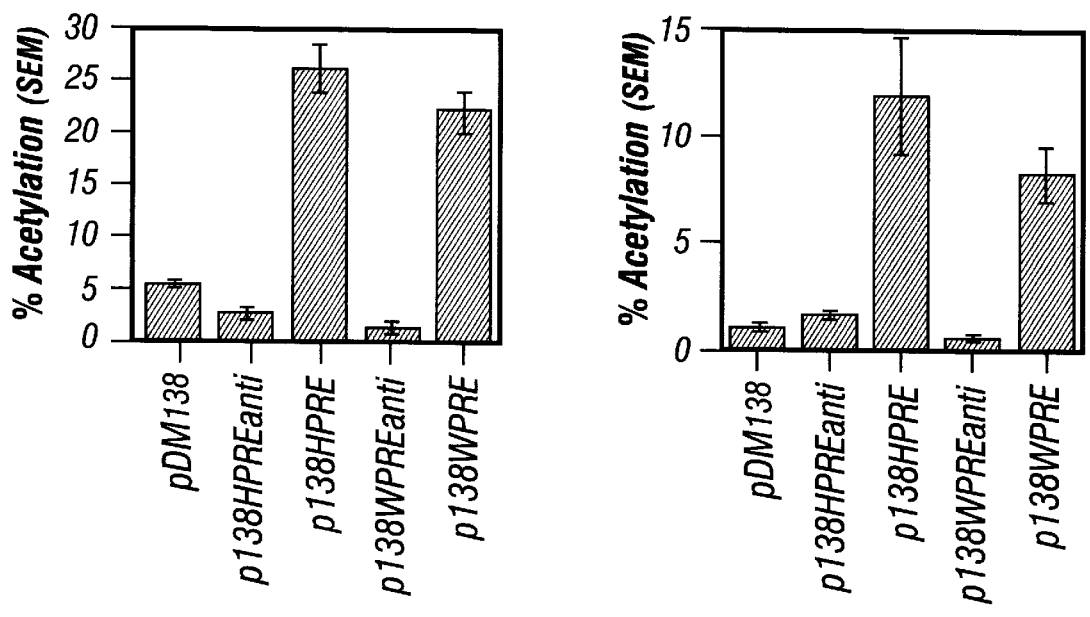

To address whether the observed differences were tissue specific, p138WPRE(900–1800) and p138HPRE (963–1684) were transiently transfected into human HepG2 and chicken LMH cells. The results, shown in FIG. 2C, differ from the effects observed in the non-liver cells. In HepG2 liver cells, p138WPRE(900–1800) was approximately 85% percent as active as p 138HPRE(963–1684). Similar results were observed in chicken liver hepatoma-derived (LMH) cells, within which p138WPRE(900–1800) possessed approximately 70% of p138HPRE(963–1684) activity.

Although it has been reported that WHV lacks enhancer I, the region homologous to the HBV enhancer I has not yet been tested in non-liver cell types. To ascertain the effect of the enhancer, the PREα from both viruses were placed in the antisense orientation upstream of a SV40 promoter driving transcription of a firefly luciferase reporter (FIG. 3A). These constructs were transiently transfected into CV1 and HepG2 cells, which were subsequently assayed for luciferase activity. FIG. 3B illustrates that, in CV1 cells, the HPRE induced a 2.2 fold increase in transcription while the WPRE increased transcription by 1.1 fold. In HepG2 cells the HPRE induced a 6.9 fold increase in transcription while the WPRE increased transcription by 1.4 fold. Similar effects were observed when the PREα were placed in the sense orientation downstream of the pGL3 polyadenylation signal (data not shown). These results confirm that putative WHV enhancer I does not display enhancer activity in liver or non-liver cells. These results also suggest that the stronger activity of the WPRE in non-liver fibroblasts is not due to a transcription enhancer.

Figure 4A:
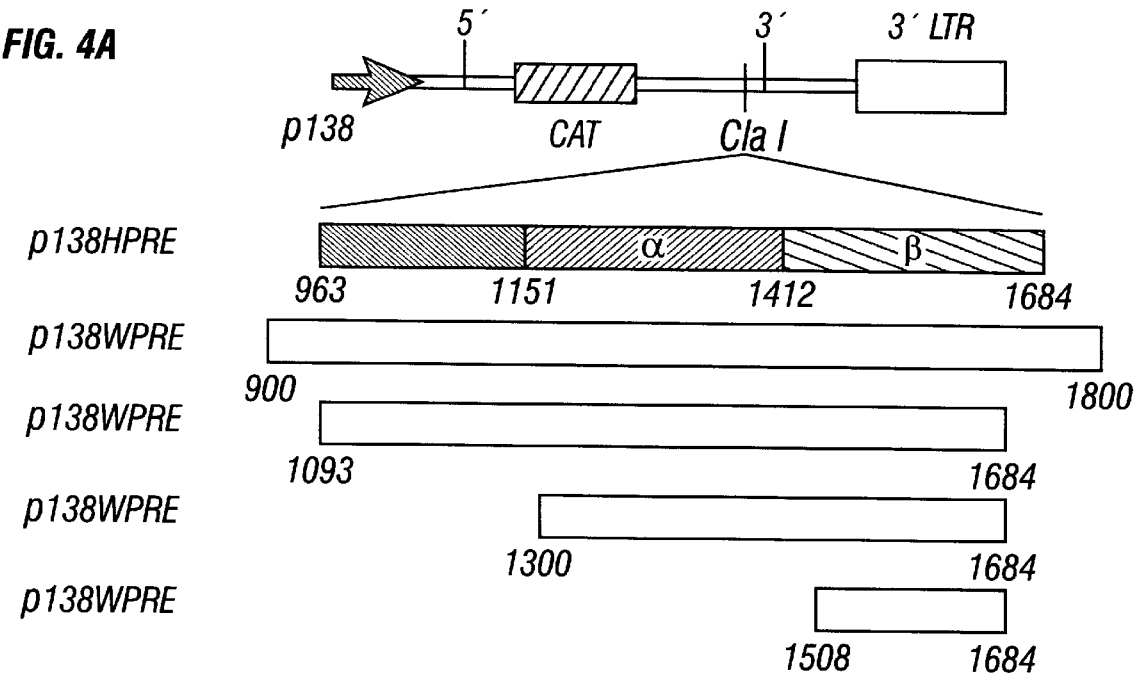
FIGS. 4A and 4B show 5' Deletion analysis of WPRE.
Figure 4B:
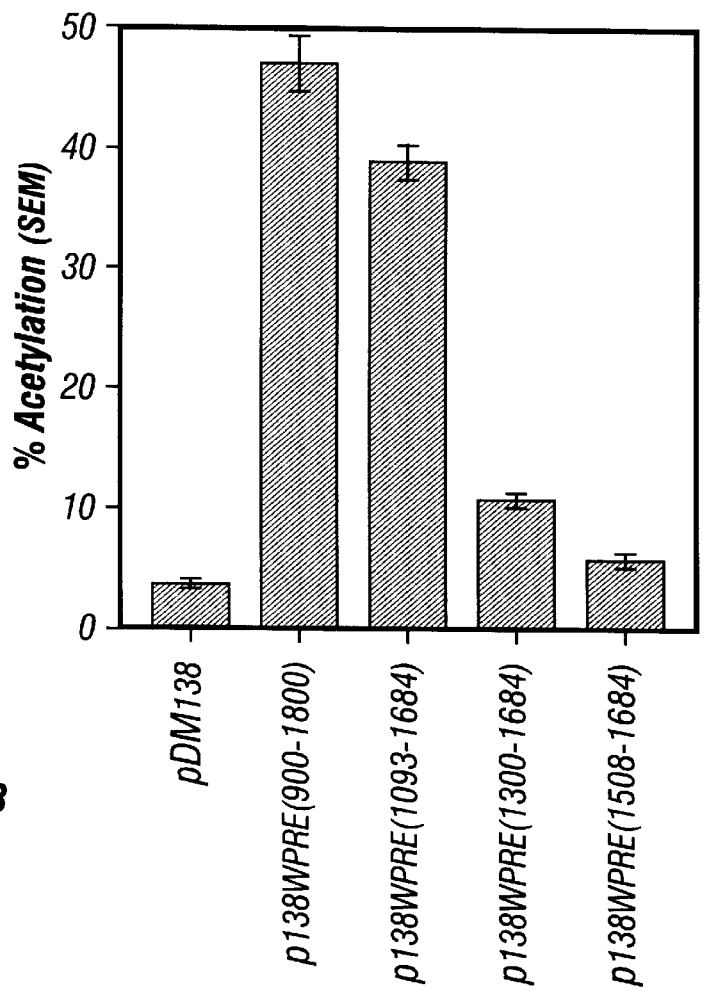

To determine whether the WPRE is posttranscriptionally stronger due to structural modifications, a 5' deletion analysis of the WPRE was performed in the pDM138 reporter assay. The WPRE 5' deletions are schematically shown, relative to the HPRE, in FIG. 4A. FIG. 4B demonstrates that p138WPRE(1093–1684) possesses 85% the activity of p138WPRE(900–1800), while p138WPRE(1300–1684) is only 22% as active as p138WPRE (900–1800). Another 5' deletion, p138WPRE(1508–1684), is 12% as active as p138WPRE(900–1800). The low activity level of p138WPRE(1508–1684) indicates that nucleotides 1508–1682 encompass a sub-element, termed WPREβ, that is homologous to the HPREβ sub-element. The data demonstrate that the WPRE is contained within WHV nucleotides 1093–1684, which shares 63.6% nucleotide identity with HBV. Studies in our laboratory have shown that the HPRE is within nucleotides 1151–1584, which are equivalent to WHV nucleotides 1281–1714 (G. Smith et al., manuscript in preparation). These results suggest that the 5' end, specifically nucleotides 1093–1250, of the WPRE is significantly different from that of the HPRE.

To map further the gross structure of the WPRE, 3' WPRE deletions were constructed. These constructs, depicted schematically relative to the HPRE in FIG. 5A, were transiently transfected into CV1 cells. The results, shown in FIG. 5B, illustrate that p138WPRE(1093–1508) is 30% as active as p138WPRE(1093–1684). p138WPRE(1093–1250), which does not contain the regions homologous to HPREα or the core enhancer I domain, was approximately 9% as active as p138WPRE(1093–1684). The 30% activity of p138WPRE (1093–1508) is similar to the activity level of the two sub-element HPRE, suggesting that WPRE 1093–1508 contains two sub-elements. One sub-element within nucleotides 1093–1508 is most likely the WHV homolog of HPREα. The other sub-element, termed WPREγ, is encompassed by nucleotides 1093–1250. These results suggest that the WPRE consists of three minimal sub-elements.

The increased WPRE activity may be due to one of the three sub-elements possessing markedly greater activity than either HPREα a or HPREβ. To test this possibility, CV1 cells were transiently transfected with the constructs depicted schematically in FIG. 6A. The results, shown in FIG. 6B, illustrate that p138HPRE(963–1684) was 39% as active as p138WPRE. The p138HPREα and p138HPREβ possess approximately 12% of p138WPRE activity. The p138WPREα, p138WPREβ and p138WPREγ sub-elements were also approximately 12% as active as p138WPRE. These data suggest that the increased WPRE activity is not due to the presence of an especially strong sub-element but is instead due to the proper presentation of the three sub-elements together.

The functional conservation of PREα and PREβ within HBV and WHV suggests that the structure of these sub-elements is also conserved. To highlight the conserved and variable regions of the PRE, the sequences of 22 HBV, 5 WHV and 2 Ground Squirrel Hepatitis (GSHV) isolates were manually aligned. A phylogentic comparative analysis highlighted two covarying base pairs between HBV and WHV and one covarying base pair between WHV and GSHV in the WPREα region. Specifically, a C-G base pair between WHV nucleotides 1428 and 1443 changes to a U-A base pair in both HBV and GSHV. In addition, a U-A base pair between WHV nucleotides 1432 and 1440 changes to an A-U base pair in HBV. An RNA secondary structure prediction algorithm, Mulfold, was used to generate secondary structure models of WHV nucleotides 1381–1487 (Jaeger et al., 1989). The secondary structure model, presented in FIG. 7A, consists of an extended stem loop with a Cr -residue bulge 3 base pairs from a 5 base loop. The predicted WPREα secondary structure has a free energy of –37.9. The covarying nucleotides are base paired in the predicted secondary structure model, suggesting that the distal stem-loop is biologically relevant. The covarying nucleotides are also based paired in the predicted secondary structure models of HPREα.

The above data suggest that the presence of a third sub-element in the WPRE increases the posttranscriptional activity relative to the bipartite HPRE. To test whether mutating a single sub-element would reduce WPRE activity to HPRE levels, the predicted WPREα stem loop structure was disrupted by mutating the C residues at nucleotides 1429 and 1431 to G residues to create p138WPREmCC1 (FIG. 7A). In addition, to test whether the predicted stem loop structure encompassed the entire WPREα, nucleotides 1396–1475 was inserted into the pDM138 vector (p138WPREamin). CV1 cells were transiently transfected with the reporters shown in FIG. 7B and the results are shown in FIG. 7C. Consistent with previous experiments, p138HPRE(963–1684) was 41% as active as p138WPRE (1093–1684). The export activity of p138WPRE mCCl, 57% of the WPRE activity, was closer to the activity of the bipartite HPRE. p138WPREα(1300–1507) and p138WPREamin(1396–1475) were both 9% as active as the WPRE. The data argue that nucleotides 1396–1475 is sufficient for WPREα activity and disruption of the predicted stem loop structure decreases WPRE activity over 40%.

These data suggest that the posttranscriptional activity of the hepadnaviral PREs can be modified by the number of sub-elements present within the RNA. To test whether the sub-elements of WPRE and HPRE are interchangeable, WPRE and HPRE chimeras were constructed. These constructs, depicted schematically in FIG. 8A, were transiently transfected into CV1 cells which were subsequently assayed for CAT activity. In this experiment, shown in FIG. 8B, p138HPRE(963–1684) was 41% as active as p138WPRE(1093–1684). The p138HPREα/WPREβ chimera was 27% as active as WPRE, while the p138WPREγα/HPREβ chimera was 76% as active as p138WPRE. These results suggest that an export element containing three posttranscriptional sub-elements, WPREγα/HPREβ, is stronger than a bipartite element. These results also indicate that the presentation of the sub-elements is also an important determinant of the elements export strength.

To test whether the presentation of three sub-elements can compensate, in liver cells, for the lack of HBV enhancer I, the chimeras described above were transiently transfected into HepG2 cells. The results are shown in FIG. 8C. p138WPRE was 85% as active as p138HPRE. Compared to p138HRE, p138HPREα/WPREβ and p138WPREγα/HPREβ were 101% and 75% as active, respectively. The strongest elements were the HPRE and the HPREα/WPREβ chimera, both of which contain two sub-elements and enhancer I. The reporters consisting of three sub-elements achieved slightly lower levels of CAT expression which argues that similar expression levels can be achieved by a combination of transcription and export or export alone.

Figure 9A:
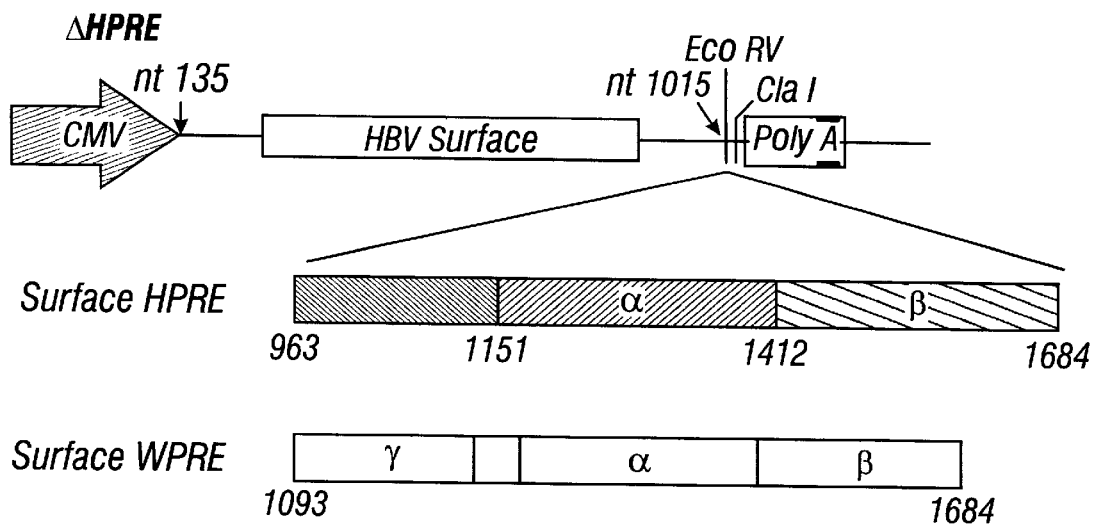
FIGS. 9A and 9B show that WPRE can replace the HPRE in the HBV Surface expression construct.
Figure 9B:
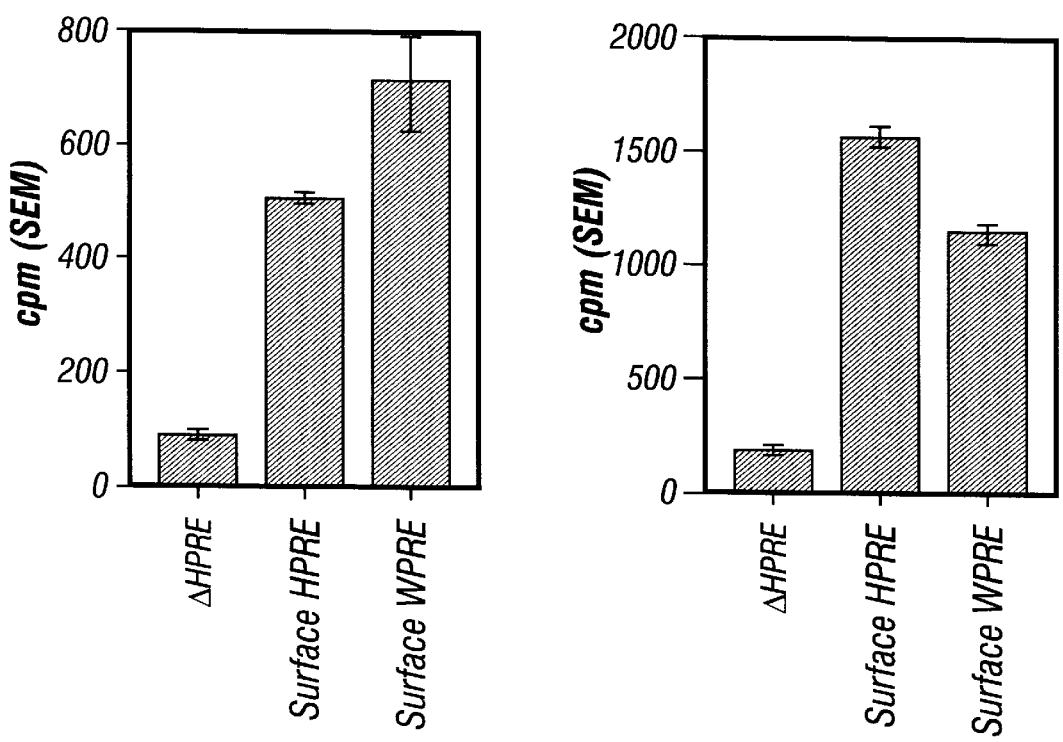

To determine whether the WPRE can substitute for the HPRE in the more natural context of HBV Surface expression, the HPRE and WPRE fragments were cloned into the Surface expression construct depicted in FIG. 9A. The results from transfected CV1 cells are shown in FIG. 9B. The ΔHPRE construct produced a low level of Surface protein expression. Surface protein expression by the Surface-HPRE construct was 6.1 fold over ΔHPRE levels while the Surface-WPRE construct induced a 8.6 fold increase in the amount of Surface protein expression. These results demonstrate that the WPRE can replace the HPRE in the Surface expression construct. Although the WPRE displays a stronger activity than the HPRE, the effect is smaller than the differences observed in the pDM138 assay.

To test whether the WPRE can restore Surface expression to levels similar to HPRE-mediated Surface expression in liver cells, HepG2 cells were transiently transfected with the constructs depicted in FIG. 9A. The results, presented in FIG. 9C, show that the HPRE can induce a 9.6-fold increase in Surface expression. The WPRE induces a 7 fold increase in Surface expression. These results are consistent with the effects observed in the pDM138 assay. The data also support the hypothesis that a strong posttranscriptional element can compensate for the lack of a transcriptional enhancer.

EXAMPLE 3

Figure 10A:
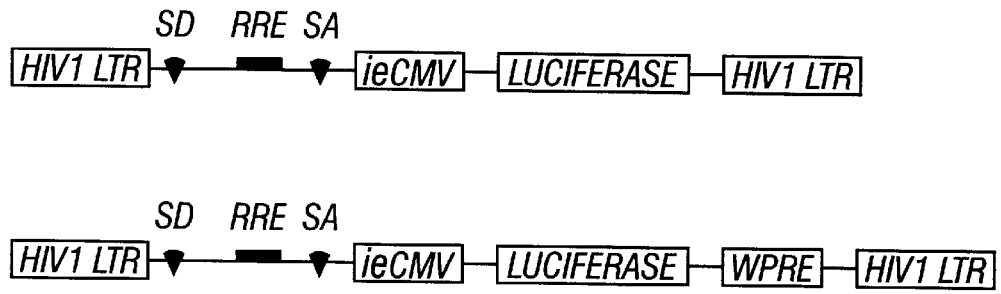
FIGS. 10A, 10B, and 10C are a schematic of vectors utilized to study the effects of WPRE on luciferase transgene expression and is a schematic of MLV vectors utilized to study the effects of WPRE on luciferase transgene expression.
Figure 10B:
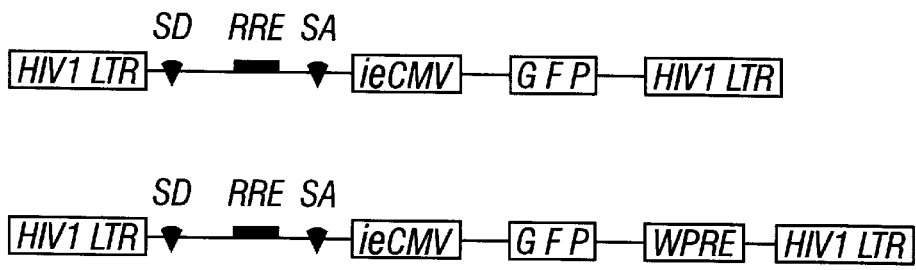
Figure 10C:
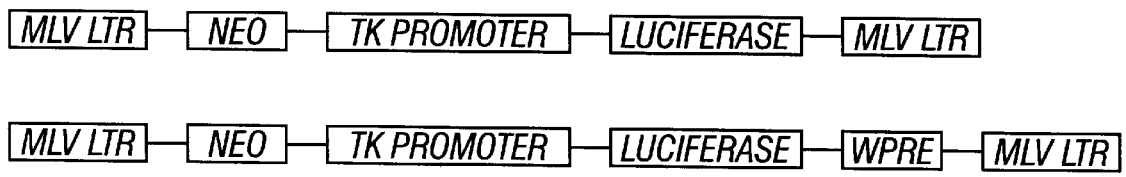

HIV or MLV-based vectors were produced to perform assays to assess WPRE activity. FIG. 10 is a schematic illustration of HIV-based transducing vectors. FIG. 10A shows the luciferase vectors and FIG. 10B shows the GFP vectors. FIG. 10C is a schematic illustration of MLV-based transducing vectors. Luciferase and GFP assays were performed as follows. Transfected or transduced cells were washed 2× with TBS (50 mM Tris pH 7.8, 130 mM NaCl, 10 mM KCl, and 5 mM MgCL2). Cells were then directly lysed and the plate was scraped with 200 uL of TBS with 0.5% NP-40. Lysates were transferred to eppendorf tubes and pelleted by centrifugation. 50 ul of the cell lysate was then mixed with 150 ul of freshly made luciferase cocktail (75 mM Tris pH 7.8, 15 mM MgOAc, and 4 mM ATP). For transfection analysis, the amount of extract assayed was normalized utilizing the expression of a co-transfected beta-galactosidase internal control. Luciferase activity was then determined utilizing a Moonlight 2010 luminometer (Analytical Luminescence Laboratory). 293T Cells were plated into six well dishes and infected with the different retroviral vector derivatives at a multiplicity of infection of approximately 0.1. 48 hrs. after transduction the cells were washed 3× with PBS and then fixed with freshly made PBS/4% paraformaldehyde. Cells were then incubated in this solution for 30 minutes followed by 2× washing with PBS. GFP fluorescence was visualized by standard microscopy techniques. Images were captured with a 8-bit analog video camera using the IPLab Scientific Image Processing System 3.1.1c (Signal Analytics). 48 hours after transduction under the conditions described above, cells were washed 3× with PBS and then harvested with 1× trypsin/EDTA. The cells were then washed 2× with PBS and then fixed by incubation with freshly made PBS/4% paraformaldehyde. The fixed cells were then characterized utilizing a flow cytometer (Beckman).

The production of pseudotyped, HIV-1-based vector particles by cotransfection of three plasmids into 293T cells has been described previously (Naldini, L., et al., Science 272, 263–267, 1996; Naldini, L., et al. Proc. Natl Acad. Sci. U.S.A. 93, 11382–11388, 1996). The original system includes: i) a packaging construct, in which the CMV immediate early promoter drives the synthesis of all HIV-1 proteins besides envelope; ii) a plasmid producing an envelope, for instance the G protein of VSV in the experiments described here; and iii) the vector itself, in which an expression cassette for the transgene is flanked by the HIV-1-derived cis-acting sequences necessary for packaging, reverse transcription and integration.

High titer stocks of lentiviral vectors carrying a CMV-driven LacZ gene, packaged with either wild-type or multiply attenuated HIV-derived constructs and pseudotyped with VSV G envelope, were prepared by transient transfection of 293T cells as previously described (Naldini et al., supra) and stored at −80° C. Prior to injection, vectors were resuspended by slow vortexing 4 hrs at room temperature, and adjusted to a p24 concentration of 1.5 mg/ml, corresponding to a titer of 1.8×10$^9$ transducing units/mi on HeLa. Vector stocks were tested for the absence of replication-competent HIV-derived virus as described in Naldini et al., supra.

All in vitro transductions were done in 6-well plates, according to previously described protocols (Naldini et al., supra). Multiplicity of infection for 293T cells was approximately 0.01 when 1 ng of p24 was used, as previously determined with a β-Gal expression vector. 293T cell were transduced in parallel with 5 ml of supernatant. Proteins were extracted for the luciferase assay 72 hours post-infection.

Figure 11A:
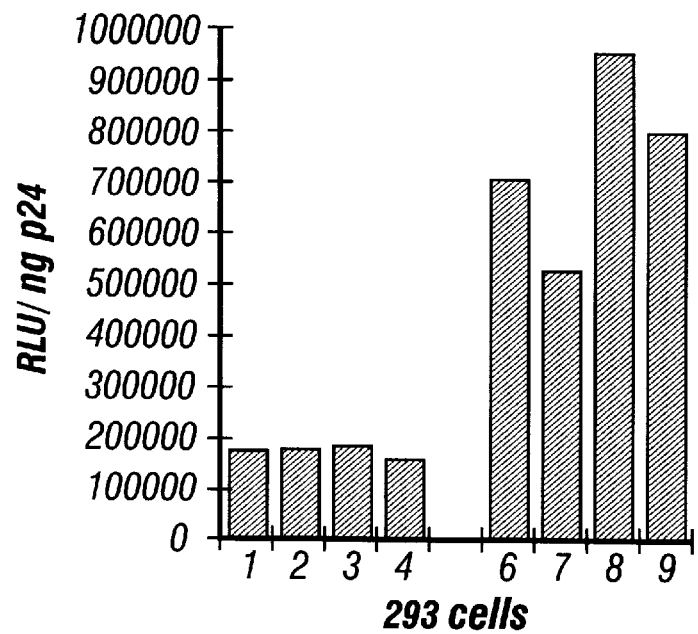
FIG. 11A is an example of a luciferase assay. Virus generated by four independent transfections were tested in 293 cells. Lanes 1–4 utilize conventional vector while lanes 6–9 are virus containing the WPRE export element.
Figure 11B:
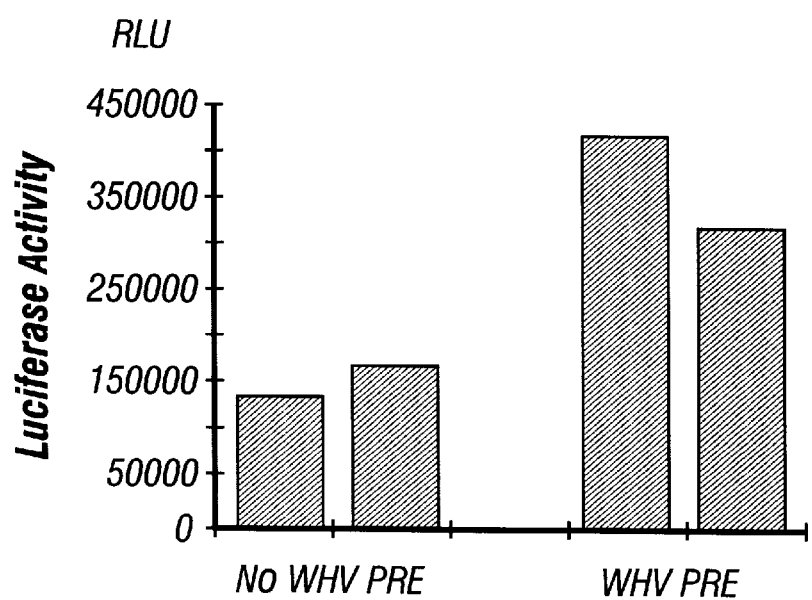
FIG. 11B shows results from MLV-based vectors containing or not containing the WPRE. The results were produced by transient transfection of 293T cells in duplicate. 100 μl of each supernatant were used to transduce in duplicate $10^5$ 293T cells. Luciferase activity was assayed 48 hours post infection. The luciferase gene is under the transcriptional control of the thymidine kinase (TK) promoter.

FIG. 11 is an example of results obtained with the luciferase assay using the HIV vector. Virus generated by four independent transfections were tested in 293 cells and shown in FIG. 11A. Lanes 14 utilize conventional vector while lanes 6–9 are virus containing the WPRE export element. The results show a substantial enhancement of expression in the presence of the WPRE. FIG. 11B shows similar results using the MLV-based luciferase viral vector.

Figure 12:
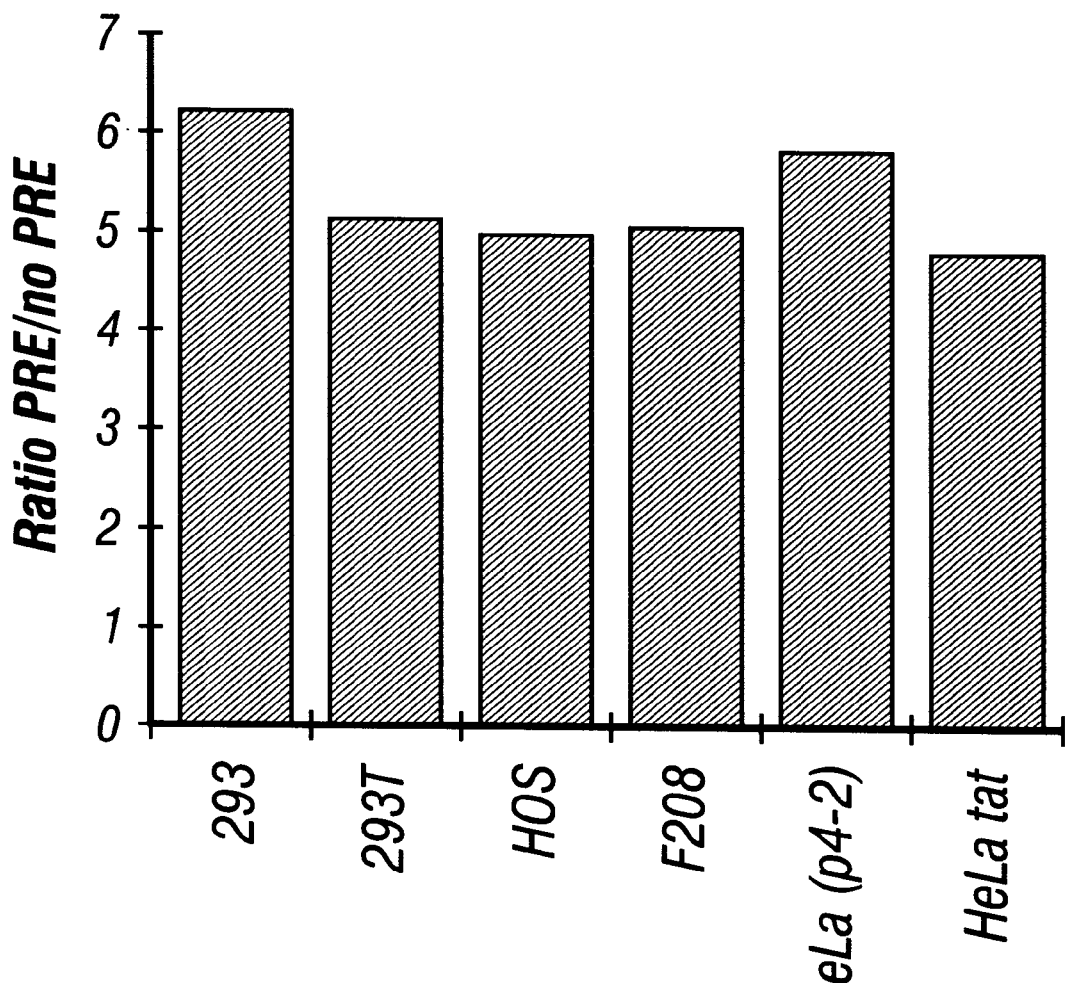
FIG. 12 shows activity of the WPRE in different cell lines. Results are shown as the ratio of luciferase expression with vector containing PRE versus normal vector.

FIG. 12 shows activity of the WPRE in different cell lines. Results are shown as the ratio of luciferase expression with vector containing PRE versus normal vector.

Figure 13A:
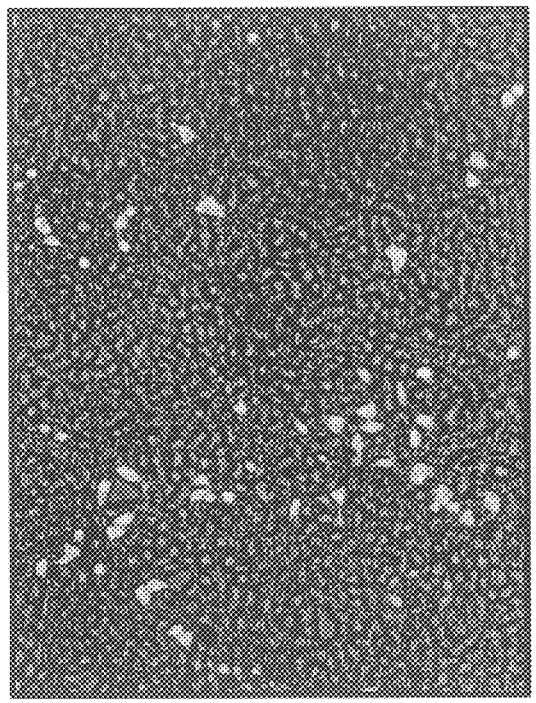
FIGS. 13A–13C show expression of the GFP gene which is enhanced by WPRE. HIV-1 based retroviral vector containing or not containing the WHV PRE were produced as described (Zufferey et al., Nature Biotechnology 15, 871 (1997).
Figure 13A:
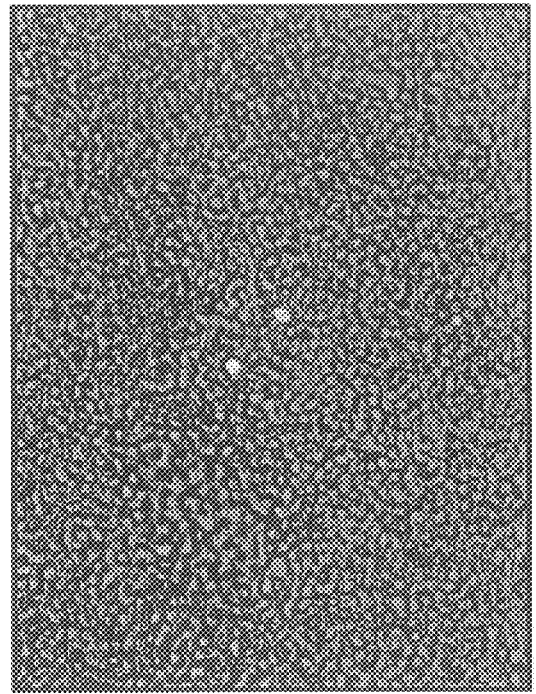
Figure 13B:
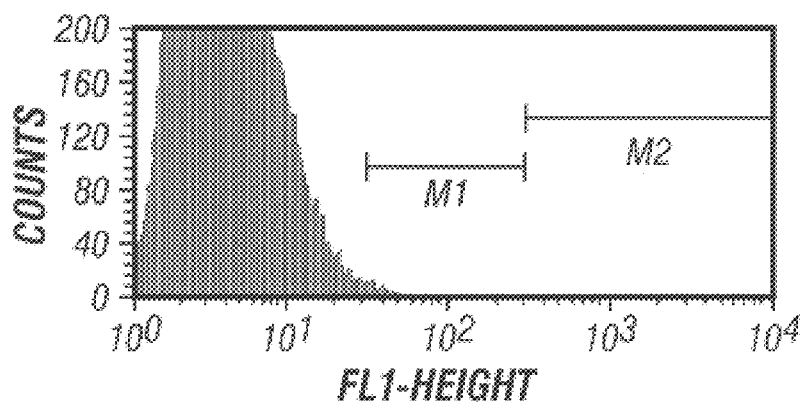
Figure 13B:
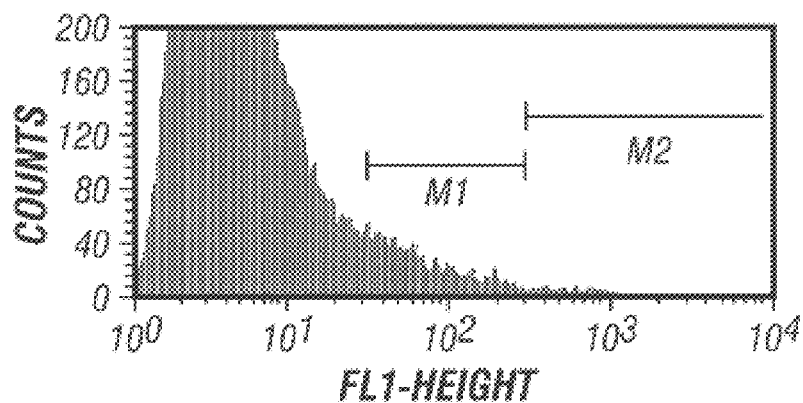
Figure 13B:
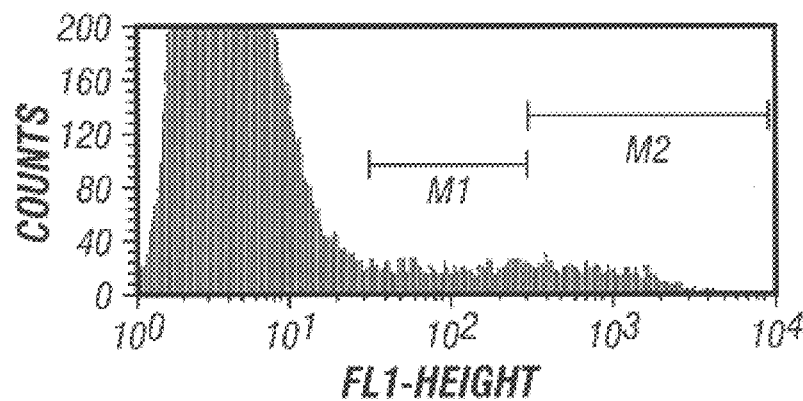
Figure 13C:
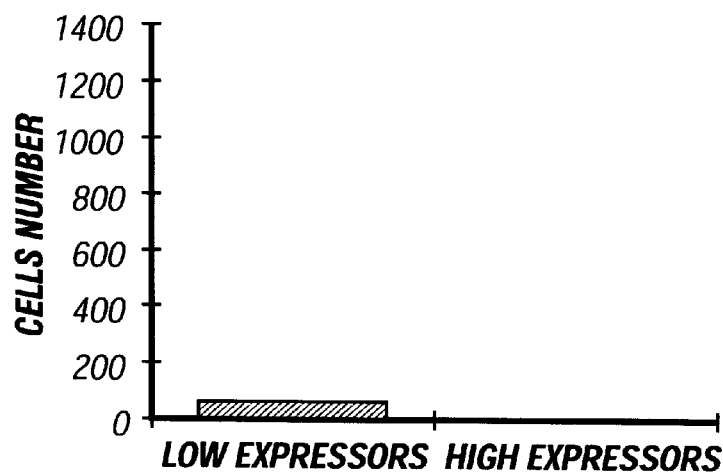
Figure 13C:
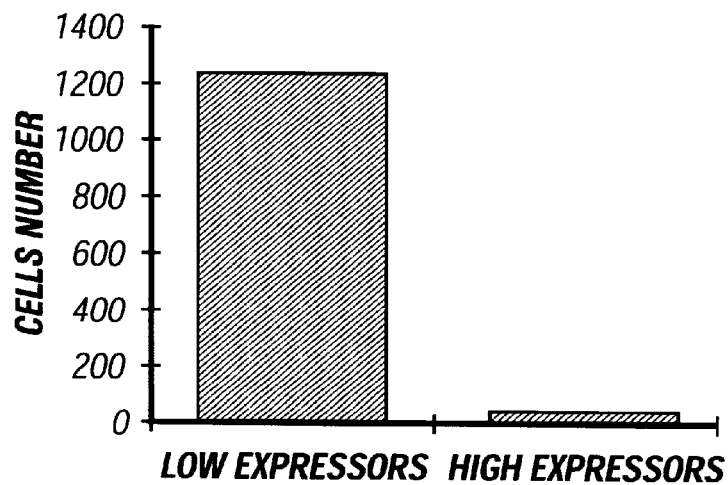
Figure 13C:
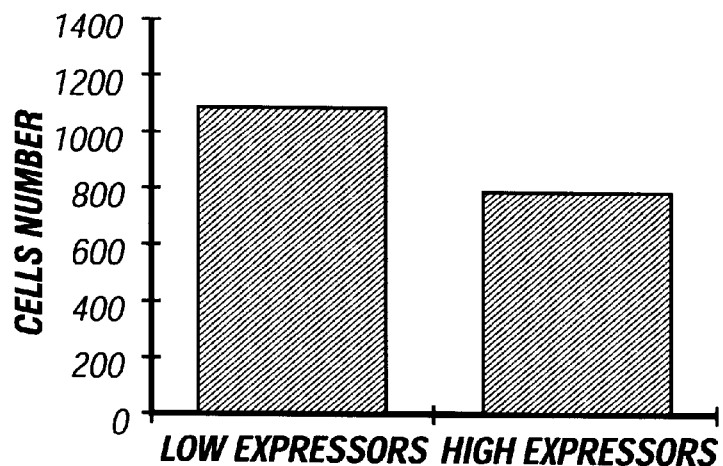

FIG. 13A–C shows expression of the GFP gene which is enhanced by WPRE. HIV-1 based retroviral vector containing or not containing the WHV PRE were produced as described (Zufferey et al., Nature Biotechnology 15, 871 (1997). FIG. 13A shows results from 293T cells transduced with both types of vector by adding equivalent amounts of p24 on 10$^5$ cells. At the level of detection chosen, many more cells appear positive when the vector contains WPRE. FIG. 13B is a FACS analysis of 293T cells transduced as in FIG. 13A. The three histograms correspond to non-transduced cells (top), cells transduced with a vector not containing WPRE (middle) or containing WPRE (bottom). The enhanced expression of GFP is reflected by the high number of cells scoring above 2×10$^2$ on the fluorescence scale. FIG. 13C is a graphic representation of the histograms shown in FIG. 13B. High expressors are defined as cells scoring above 2×10$^2$ on the fluorescence scale in FIG. 13B. The number of high expressor is 25 times higher when the vector contains WPRE.

Although the invention has been described with reference to the presently preferred embodiment, it should be understood that various modifications can be made without departing from the spirit of the invention. Accordingly, the invention is limited only by the following claims.

What is claimed is:

1. An isolated nucleic acid sequence which comprises a cis-acting RNA export element which mediates transport of RNA from the nucleus to the cytoplasm, wherein the element is not a retroviral export element, and wherein the element is selected from the group consisting of:
   a) SEQ ID NO:1;
   b) SEQ ID NO:1, which is an RNA sequence;
   c) nucleic acid sequences fully complementary to the complete individual strands of the sequence of a) or b); and
   d) fragments of a), b), or c) which are at least 15 nucleotides in length.

2. A nucleic acid sequence of claim 1, operably linked to a heterologous nucleic acid sequence.

3. The nucleic acid sequence of claim 2, wherein the heterologous nucleic acid sequence is a DNA.

4. The nucleic acid sequence of claim 2, wherein the heterologous nucleic acid sequence is a RNA.

5. A recombinant expression vector containing the nucleic acid sequence of claim 1.

6. The vector of claim 5, wherein the vector is a virus vector.

7. The vector of claim 6, wherein the virus is an RNA virus.

8. The vector of claim 7, wherein the RNA virus is a retrovirus.

9. The vector of claim 6, wherein the virus is a DNA virus.

10. The vector of claim 9, wherein the DNA virus is a herpes virus.

11. The vector of claim 9, wherein the DNA virus is an adenovirus or adeno-associated virus.

12. A host cell containing the vector of claim 5.

13. The host cell of claim 12, wherein the cell is a mammalian cell.

14. The host cell of claim 12, wherein the cell is a plant cell.

* * * * *